(12) United States Patent
Mukai

(10) Patent No.: US 11,129,758 B2
(45) Date of Patent: Sep. 28, 2021

(54) ABSORBENT ARTICLE

(71) Applicant: UNICHARM CORPORATION, Shikokuchuo (JP)

(72) Inventor: Hirotomo Mukai, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 449 days.

(21) Appl. No.: 16/086,606

(22) PCT Filed: Jan. 25, 2017

(86) PCT No.: PCT/JP2017/002455
§ 371 (c)(1),
(2) Date: Sep. 20, 2018

(87) PCT Pub. No.: WO2017/169027
PCT Pub. Date: Oct. 5, 2017

(65) Prior Publication Data
US 2019/0133844 A1 May 9, 2019

(30) Foreign Application Priority Data

Mar. 29, 2016 (JP) .............................. JP2016-065272

(51) Int. Cl.
*A61F 13/15* (2006.01)
*A61F 13/511* (2006.01)
(Continued)

(52) U.S. Cl.
CPC .. *A61F 13/51121* (2013.01); *A61F 13/49006* (2013.01); *A61F 13/5116* (2013.01);
(Continued)

(58) Field of Classification Search
CPC .......... A61F 13/51121; A61F 13/49006; A61F 13/51108; A61F 13/5116; A61F 13/535;
(Continued)

(56) References Cited

U.S. PATENT DOCUMENTS

2003/0167044 A1* 9/2003 Toyoshima ............ D04H 1/542
  604/367
2013/0178811 A1* 7/2013 Kikuchi ............ A61F 13/51394
  604/365

FOREIGN PATENT DOCUMENTS

CN    1498603 A    5/2004
CN  101516303 A    8/2009
(Continued)

OTHER PUBLICATIONS

International Search Report in PCT Application No. PCT/JP2017/002455, dated Apr. 18, 2017, 4pp.
(Continued)

*Primary Examiner* — Jacqueline F Stephens
(74) *Attorney, Agent, or Firm* — Hauptman Ham, LLP

(57) ABSTRACT

An absorbent article includes an absorbent core, a top sheet provided on a skin-side of a thickness direction of the absorbent core, and a second sheet arranged between the absorbent core and the top sheet in the thickness direction and to be placed in a wearer's inseam. The top sheet has a plurality of protrusions formed along a longitudinal direction and spaced apart in a horizontal direction. The second sheet is smaller than the top sheet in the horizontal direction. The top sheet has an overlapping region overlapping with the second sheet in the thickness direction and both end regions separated by a predetermined distance outward from the overlapping region in the horizontal direction and provided to overlap with the overlapping region in the longitudinal direction. A horizontal pitch of the protrusions in the overlapping region is larger than a horizontal pitch of the protrusions in the two end regions.

11 Claims, 12 Drawing Sheets

FIRST EMBODIMENT

(51) Int. Cl.
*A61F 13/539* (2006.01)
*A61F 13/535* (2006.01)
*A61F 13/49* (2006.01)
A61F 13/494 (2006.01)
A61F 13/496 (2006.01)
A61F 13/513 (2006.01)

(52) U.S. Cl.
CPC ...... *A61F 13/51108* (2013.01); *A61F 13/535* (2013.01); *A61F 13/539* (2013.01); *A61F 13/494* (2013.01); *A61F 13/4963* (2013.01); *A61F 13/513* (2013.01)

(58) Field of Classification Search
CPC .. A61F 13/539; A61F 13/494; A61F 13/4963; A61F 13/513
USPC .................. 604/379, 378, 380, 383, 385.101
See application file for complete search history.

(56) References Cited

FOREIGN PATENT DOCUMENTS

| | | |
|---|---|---|
| CN | 201701387 U | 1/2011 |
| CN | 102575398 A | 7/2012 |
| CN | 102614051 A | 8/2012 |
| CN | 103687578 A | 3/2014 |
| CN | 103690313 A | 4/2014 |
| CN | 204192873 U | 3/2015 |
| CN | 204744668 U | 11/2015 |
| JP | 2000-271170 A | 10/2000 |
| JP | 2004-166831 A | 6/2004 |
| JP | 2006-299480 A | 11/2006 |
| JP | 2009-291473 A | 12/2009 |
| JP | 2012-75638 A | 4/2012 |
| JP | 2012-75663 A | 4/2012 |
| JP | 2013-169388 A | 9/2013 |
| WO | 2012043842 A1 | 4/2012 |
| WO | 2014/068487 A1 | 5/2014 |
| WO | 2014/196670 A1 | 12/2014 |
| WO | 2015/015969 A1 | 2/2015 |

OTHER PUBLICATIONS

Extended European Search Report in EP Application No. 17773577.6, dated Mar. 14, 2019, 6pp.
International Preliminary Report on Patentability in PCT Application No. PCT/JP2017/002455, dated Apr. 18, 2017, 18pp.
Office Action in CN Application No. 201780021558.X, dated Sep. 8, 2020, 9pp.

\* cited by examiner

FIRST EMBODIMENT

FIRST EMBODIMENT

FIRST EMBODIMENT

FIRST EMBODIMENT

FIRST EMBODIMENT

ABSORBENT ARTICLE

RELATED APPLICATIONS

The present application is a National Phase of PCT/JP2017/002455, filed Jan. 25, 2017, and claims priority based on Japanese Patent Application No. 2016-065272, filed Mar. 29, 2016.

TECHNICAL FIELD

The present invention relates to an absorbent article.

BACKGROUND ART

A pull-on disposable diaper as an absorbent article is known. For example, Patent Document 1 discloses an absorbent article having a front exterior member, a back exterior member, and an absorbent main body crosslinking between the front exterior member and the back exterior member, wherein both horizontal edges of the front exterior member and both horizontal edges of the back exterior member are bonded to each other to form a waist opening and a pair of leg openings.

In this diaper, a top sheet of the absorbent main body has a plurality of concave portions hollowed in a non-skin side and a plurality of convex portions protruding in a skin side. A plurality of concave portions and a plurality of convex portions alternate in a horizontal direction (short direction) of the top sheet. By employing such an uneven sheet provided with concave and convex portions in the top sheet, solid components (impurities) in urine are filtered out. Therefore, it is possible to suppress clogging of the absorbent main body caused by solid components and prevent leakage of urine.

CITATION LIST

Patent Documents

[Patent Document 1] JP-A-2013-169388

SUMMARY

Technical Problem

However, in the diaper discussed in Patent Document 1, if a force is exerted on the top sheet to compress (squeeze) the convex portions in a horizontal direction, gaps between fibers of the convex portions are narrowed, and clogging is easily generated. Meanwhile, if a pitch between the convex portions adjacent in the horizontal direction is adjusted to prevent the clogging, a clearance is easily formed between the diaper and the wearer's skin. This may degrade the fit.

In view of the aforementioned problems, it is therefore an object of the present invention to provide an absorbent article capable of improving fit while suppressing leakage of urine, menstrual bleeding, and the like.

Solution to Problem

According to an aspect of the invention, there is provided an absorbent article having a longitudinal direction, a horizontal direction, and a thickness direction, including: an absorbent core to absorb a liquid; a liquid permeable skin-side sheet provided on a skin side of the absorbent core in the thickness direction; and a liquid permeable second sheet arranged between the absorbent core and the skin-side sheet in the thickness direction and to be placed in a wearer's inseam, wherein the skin-side sheet has a plurality of protrusions formed along the longitudinal direction and spaced apart in the horizontal direction, the second sheet is smaller than the skin-side sheet in the horizontal direction, the skin-side sheet has an overlapping region overlapping with the second sheet in the thickness direction, and both end regions separated by a predetermined distance outward from the overlapping region in the horizontal direction and provided to overlap with the overlapping region in the longitudinal direction, and a horizontal pitch of the protrusions in the overlapping region of the skin-side sheet is larger than a horizontal pitch of the protrusions in the two end regions of the skin-side sheet. Other features and advantages of the invention will become apparent by reading the following specification with reference to the attached drawings.

Advantageous Effects

According to the present invention, it is possible to improve fit while suppressing leakage of urine, menstrual bleeding, and the like.

BRIEF DESCRIPTION OF DRAWINGS

FIGS. 9A, 9B, 9C, and 9D are schematic cross-sectional views illustrating the top sheet in a thickness direction, in which FIG. 9A illustrates a P1 portion of FIG. 8A, FIG. 9B illustrates a P2 portion of FIG. 8B, FIG. 9C illustrates a P3 portion of FIG. 8B, and FIG. 9D illustrates a P4 portion of FIG. 8B.

DESCRIPTION OF EMBODIMENTS

Figure 1:
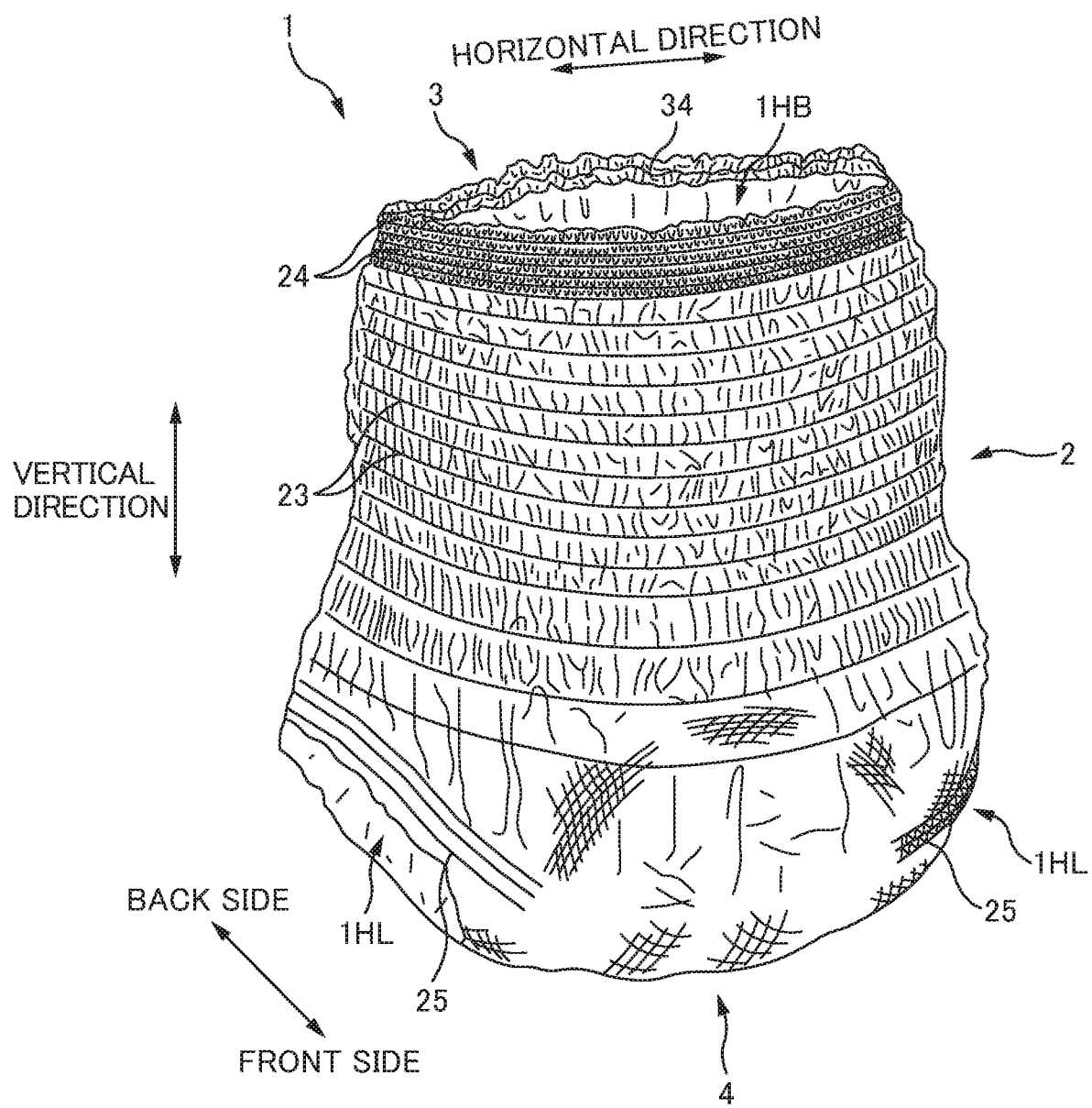
FIG. 1 is a schematic perspective view illustrating an exemplary configuration of a diaper according to a first embodiment of the invention.

At least the following features will be clearly understood from the specification and the accompanying drawings.

An absorbent article having a longitudinal direction, a horizontal direction, and a thickness direction, includes: an absorbent core to absorb a liquid; a liquid permeable skin-side sheet provided on a skin side of the absorbent core in the thickness direction; and a liquid permeable second sheet arranged between the absorbent core and the skin-side sheet in the thickness direction and to be placed in a wearer's inseam, wherein the skin-side sheet has a plurality of protrusions formed along the longitudinal direction and spaced apart in the horizontal direction, the second sheet is smaller than the skin-side sheet in the horizontal direction, the skin-side sheet has an overlapping region overlapping with the second sheet in the thickness direction, and two end regions separated by a predetermined distance outward from the overlapping region in the horizontal direction and provided to overlap with the overlapping region in the longitudinal direction, wherein a horizontal pitch of the protrusions in the overlapping region of the skin-side sheet is larger than a horizontal pitch of the protrusions in the two end regions of the skin-side sheet.

In such an absorbent article, in the overlapping region of the skin-side sheet overlapping with the second sheet in the thickness direction, the protrusions are not easily compressed (squeezed) in the horizontal direction due to stiffness of the second sheet. Therefore, it is possible to easily maintain the shapes of the protrusions. As a result, in the overlapping region placed under a wearer's excretory opening, it is possible to suppress clogging of the skin-side sheet caused by solid components in urine, menstrual bleeding, and the like. In addition, in both end regions close to the wearer's leg, a horizontal pitch of the protrusions is smaller than a horizontal pitch of the protrusions in the overlapping region. Therefore, the number of gaps of the protrusions adjacent in the horizontal direction per unit length is larger than the number of gaps of the adjacent protrusions per unit length of the overlapping region. The gap between the protrusions adjacent in the horizontal direction is smaller than the thickness of the protrusion. Therefore, the skin-side sheet is easily deformable the thickness direction. Accordingly, in both end regions, the diaper is easily deformable the thickness direction and easily deforms to fit the shape of the wearer's inseam, compared to the overlapping region.

Therefore, by maintaining the shapes of a plurality of protrusions in a region close to the excretory opening, it is possible to suppress clogging caused by solid components in urine, menstrual bleeding, and the like and prevent leakage of urine, menstrual bleeding, and the like. In addition, it is possible to improve fit by fitting the diaper to a wearer's somatotype in the vicinity of the legs.

In the absorbent article described above, preferably, the horizontal pitch of the protrusions gradually increases from the two end regions toward the overlapping region in the skin-side sheet.

In such an absorbent article, the horizontal pitch of the protrusions gradually increases from both end regions toward the overlapping region in the skin-side sheet. Therefore, even in both sides of the overlapping region of the horizontal direction, it is possible to easily maintain the shape of the protrusion in a portion close to the overlapping region and easily filter out solid components in urine, menstrual bleeding, and the like. In addition, toward both end regions, the number of gaps of the protrusions adjacent in the horizontal direction per unit length increases more than the number of gaps of the protrusions adjacent in the horizontal direction per unit length of the overlapping region. Therefore, it is possible to facilitate collapse in the thickness direction compared to the overlapping region and improve the fit.

In the absorbent article described above, preferably, the skin-side sheet is compressed in the horizontal direction, and horizontal compression per unit length of the skin-side sheet in the overlapping region is smaller than compression per unit length of the skin-side sheet in the two end regions.

In such an absorbent article, the horizontal pitch of the protrusions is adjusted depending on the compression per unit length of the skin-side sheet in the horizontal direction. Therefore, it is possible to change the horizontal pitch of the protrusions, for example, without the need to change a pitch setting for nozzles of a manufacturing device.

In the absorbent article described above, preferably, the second sheet is smaller than the skin-side sheet in the longitudinal direction, and the horizontal pitch of the protrusions in the overlapping region is larger than the horizontal pitch of the protrusions in at least one of one end and the other end of the longitudinal direction of the skin-side sheet.

In such an absorbent article, in at least one of one end and the other end of the longitudinal direction of the skin-side sheet, the horizontal pitch of the protrusions is smaller than the horizontal pitch of the protrusions of the overlapping region. Therefore, the number of gaps of the protrusions adjacent in the horizontal direction per unit length is larger than the number of gaps of adjacent protrusions per unit length in the overlapping region. Since the gap between the protrusions adjacent in the horizontal direction is smaller than the thickness of the protrusion, the skin-side sheet is easily deformable the thickness direction. Therefore, in at least one of one end and the other end of the longitudinal direction of the skin-side sheet, the diaper is easily deformable the thickness direction compared to the overlapping region and easily deforms to fit the shape of the wearer's front or back side (for example, in a cup shape). As a result, even in a front waist or a back waist, it is possible to fit the diaper to a wearer's somatotype. Therefore, it is possible to improve the fit when worn.

In the absorbent article described above, preferably, the skin-side sheet has a horizontal pitch of the protrusions gradually increasing toward the overlapping region from at least one of the one end and the other end of the longitudinal direction.

In such an absorbent article, the horizontal pitch of the protrusions gradually increases toward the overlapping region from at least one of one end and the other end of the longitudinal direction of the skin-side sheet. Even in both sides of the longitudinal direction of the overlapping region, it is possible to easily maintain the shape of the protrusions in a portion close to the overlapping region and easily filter out solid components in urine, menstrual bleeding, and the like. In addition, toward one end or the other end of the longitudinal direction of the skin-side sheet, the number of gaps of the protrusions adjacent in the horizontal direction per unit length increases more than the number of gaps of the protrusions adjacent in the horizontal direction per unit length in the overlapping region. Therefore, the diaper is easily deformable the thickness direction and easily deforms to fit the shape of the wearer's front side or rear side, compared to the overlapping region. As a result, it is possible to further improve fit in the vicinity of the waist opening.

In the absorbent article described above, preferably, the skin-side sheet is compressed in the horizontal direction, and horizontal compression per unit length of the skin-side sheet in the overlapping region is smaller than longitudinal compression per unit length of the skin-side sheet in at least one of the one end and the other end.

In such an absorbent article, the horizontal pitch of the protrusions is adjusted depending on the horizontal compression per unit length of the skin-side sheet even in the longitudinal direction of the skin-side sheet. Therefore, it is possible to change the horizontal pitch of the protrusions without the need to change a pitch setting of nozzles of a manufacturing device and the like.

In the absorbent article described above, preferably, the skin-side sheet and the absorbent core are bonded in the thickness direction by a plurality of skin-side bonding portions provided at intervals in the horizontal direction between the skin-side sheet and the absorbent core, and a position horizontally intermediate between each apex of any two protrusions adjacent in the horizontal direction among the plurality of protrusions does not overlap with a position of the skin-side bonding portion of the thickness direction in the two end regions of the skin-side sheet.

In such an absorbent article, since the position horizontally intermediate between each apex of the protrusions adjacent in the horizontal direction overlaps with a position of the gap of the skin-side bonding portions adjacent in the horizontal direction in the thickness direction in the two end regions, it is possible to more easily induce the collapse of the skin-side sheet in the thickness direction. As a result, it is possible to further improve fit when worn.

Preferably, the absorbent article described above further includes a liquid non-permeable non-skin-side sheet provided on a non-skin side of the absorbent core, wherein the non-skin-side sheet and the absorbent core are bonded in the thickness direction by a plurality of non-skin-side bonding portions provided at intervals in the horizontal direction, and a position horizontally intermediate between each apex of any two protrusions adjacent in the horizontal direction among the plurality of protrusions does not overlap with a position of the non-skin-side bonding portion in the thickness direction in the two end regions of the skin-side sheet.

In such an absorbent article, in both end regions, the position horizontally intermediate between each apex of the protrusions adjacent in the horizontal direction overlaps with a position of the gap of the skin-side bonding portions adjacent in the horizontal direction and a position of the gap of the non-skin-side bonding portions adjacent in the horizontal direction in the thickness direction. Therefore, the skin-side sheet is easily deformable the thickness direction in both the gap of the skin-side bonding portion and the gap of the non-skin-side bonding portion. As a result, it is possible to further improve fit when worn.

In the absorbent article described above, preferably, the absorbent core is provided with grooves extending along the longitudinal direction in both horizontal sides of the second sheet, and a basis weight of the groove is smaller than a basis weight of a portion other than the groove of the absorbent core.

In such an absorbent article, a pair of grooves (for example, slits) having a small basis weight are provided in the absorbent core. Therefore, the absorbent core having a thickness is easily deformable the thickness direction. In addition, since such grooves are provided on both sides of the overlapping region in the horizontal direction, it is possible to fit the diaper to a wearer's somatotype in the inseam side of the wearer's legs. Accordingly, it is possible to improve fit.

In the absorbent article described above, a position horizontally intermediate between each apex of any two protrusions adjacent in the horizontal direction among the plurality of protrusions overlaps with a position of the groove in the thickness direction.

In such an absorbent article, the middle position (a portion of the skin-side sheet having a thickness smaller than the thickness of the protrusion) overlaps with a position of the groove in the thickness direction. Therefore, the skin-side sheet is easily deformable the thickness direction in the groove. As a result, it is possible to fit the diaper to a wearer's somatotype and further improve fit when worn.

In the absorbent article described above, preferably, the skin-side sheet has a density difference in the horizontal direction, and an average density of the second sheet is higher than an average density of the skin-side sheet.

In such an absorbent article, since the average density of the second sheet is higher than the average density of the skin-side sheet, urine or menstrual bleeding passing through the skin-side sheet can easily move to the second sheet. As a result, a liquid migration property in the thickness direction is improved in the overlapping region. Therefore, urine, menstrual bleeding, and the like can be easily absorbed in the absorbent core. Accordingly, it is possible to prevent urine, menstrual bleeding, and the like from accumulating on the skin-side sheet and to more effectively suppress leakage.

In the absorbent article described above, preferably, the skin-side sheet is formed of air-through nonwoven fabric.

In such an absorbent article, the skin-side sheet is formed of short fibers of air-through nonwoven fabric having a high degree of freedom without bonding. Therefore, it is possible to easily form a gap between fibers. As a result, it is possible to more effectively suppress clogging of the skin-side sheet caused by solid components in urine, menstrual bleeding, and the like.

First Embodiment

As an example of the absorbent article according to a first embodiment of the invention, a pull-on disposable diaper (hereinafter, simply referred to as "diaper 1") especially for elderly persons will be described.

(Overall Configuration of Diaper 1)

First, the overall configuration of the diaper 1 will be described with reference to FIGS. 1 to 3.

FIG. 1 is a schematic perspective view illustrating an exemplary configuration of the diaper 1 according to the first embodiment. FIG. 2 is a schematic plan view illustrating the diaper 1 in an unfolded and expanded state as seen from a skin side. FIG. 3 is a cross-sectional view along the line III-III of FIG. 2.

As illustrated in FIG. 1, the diaper 1 has a "vertical direction" and a "horizontal direction" perpendicular to the vertical direction. In addition, as illustrated in FIG. 3, the diaper 1 has a "thickness direction". Along the vertical direction, a waist side of the wearer will be referred to as an "upper side", and an inseam side of the wearer will be referred to as a "lower side". In addition, assuming that the wearer wears the diaper 1, a side at the front of the wearer will be simply referred to as a "front side", and a side at the back of the wearer will be simply referred to as a "back side". The "thickness direction" refers to a direction in which each member of the diaper 1 is stacked. In addition, assuming that the wearer wears the diaper 1, a side where a wearer makes contact with the wearer's skin will be referred to as a "skin side", and the side opposite the skin side will be referred to as a "non-skin side". In the following description, the skin side of the thickness direction will be simply referred to as a "skin side", and the non-skin side of the thickness direction will be simply referred to as the "non-skin side".

As illustrated in FIG. 1, when worn, the diaper 1 has a front waist section 2 placed at the front of the wearer, a back waist section 3 placed at the back of the wearer, and an inseam section 4. As illustrated in FIG. 2, in the diaper 1, bonding regions 20 provided in both ends of the horizontal direction of the front waist section 2, and bonding regions 30 provided in both ends of the horizontal direction of the back waist section 3 are bonded to each other, so that a single waist opening 1HB and a pair of leg openings 1HL are formed as illustrated in FIG. 1 to provide a pull-on diaper.

Figure 2:
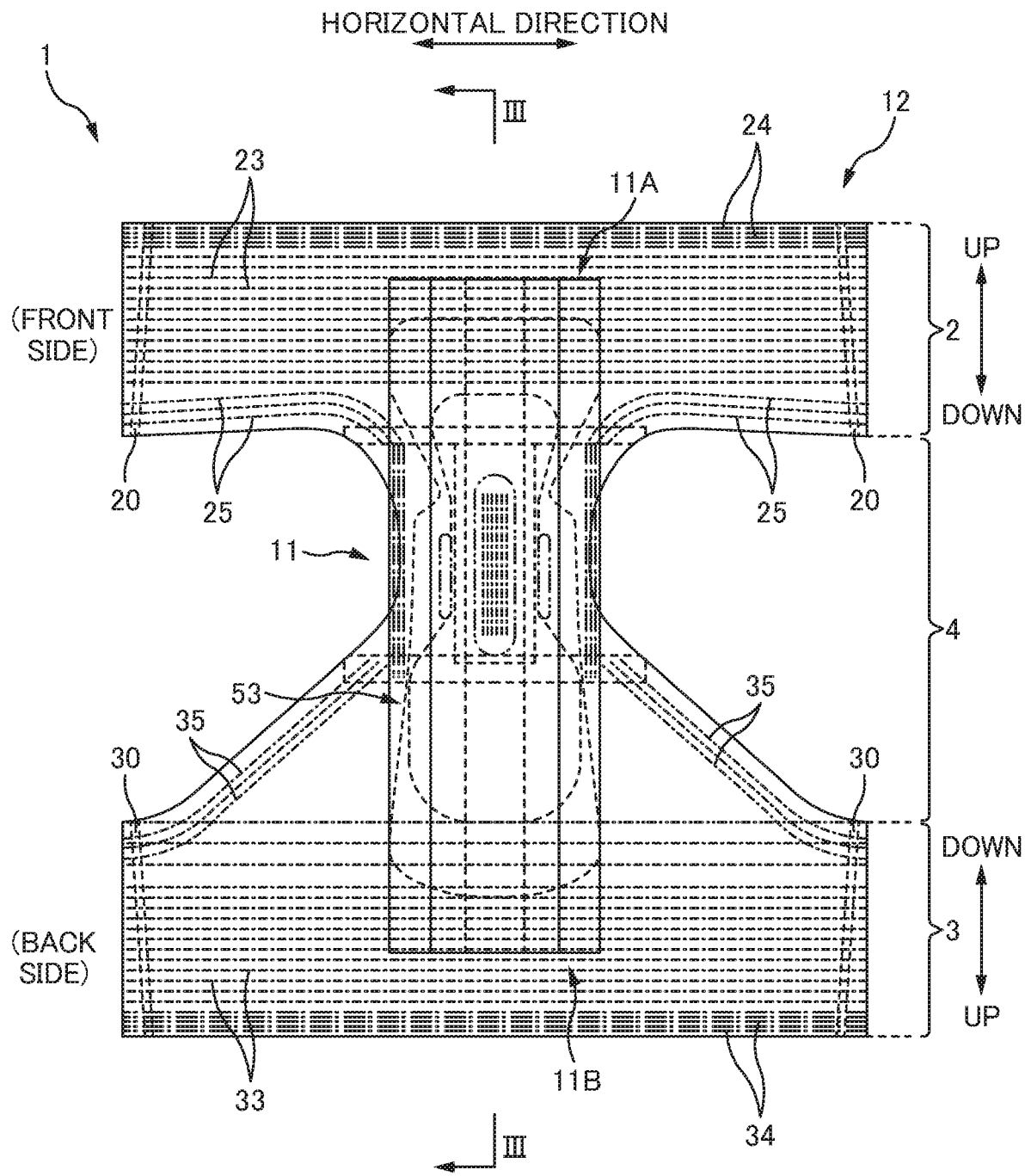
FIG. 2 is a schematic plan view illustrating a diaper in an unfolded state as seen from a skin side.
Figure 3:
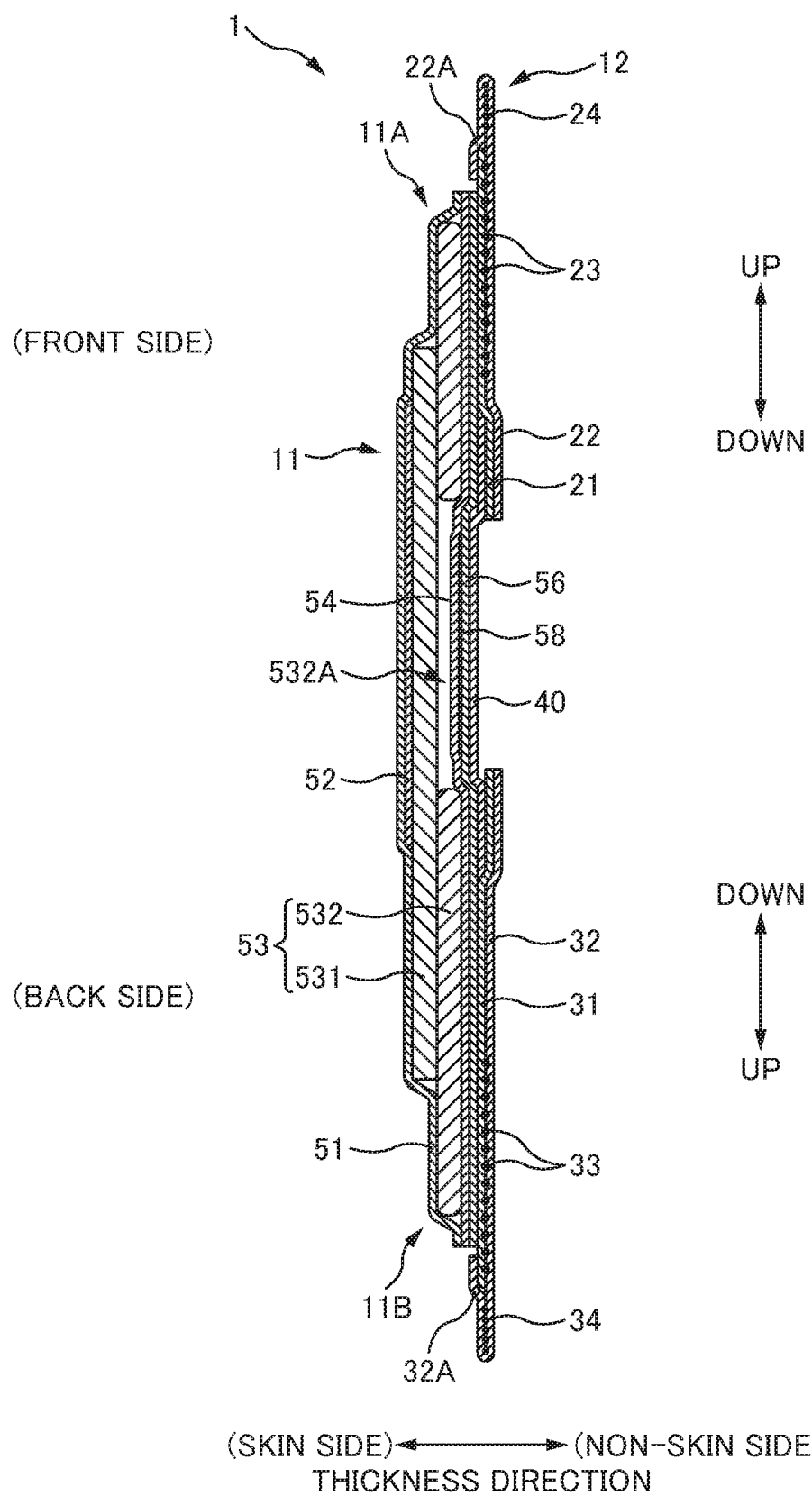
FIG. 3 is a cross-sectional view along a line III-III of FIG. 2.

According to the embodiment, as illustrated in FIGS. 2 and 3, the diaper 1 is a so-called two-piece type including a band-shaped absorbent main body 11 that absorbs liquid such as urine and an exterior member 12 on the non-skin side of the absorbent main body 11. The exterior member 12 has the front waist section 2, the back waist section 3, and the inseam section 4.

As illustrated in FIG. 2, while the diaper 1 is unfolded, the front waist section 2 is provided on one end portion 11A of the longitudinal direction of the absorbent main body 11, and the back waist section 3 is provided on the other end portion 11B of the longitudinal direction of the absorbent main body 11. That is, the absorbent main body 11 is stretched between the front waist section 2 and the back waist section 3. Similar to the absorbent main body 11, the inseam section 4 is stretched between the front waist section 2 and the back waist section 3 in the non-skin side of the absorbent main body 11.

(Configuration of Exterior Member 12)

Next, a configuration of the exterior member 12 will be described in details with reference to FIGS. 2 and 3.

As illustrated in FIG. 3, the exterior member 12 has a front exterior top sheet 21, a front exterior back sheet 22, a back exterior top sheet 31, a back exterior back sheet 32, and an exterior center sheet 40. The sheets may be formed of, for example, air-through nonwoven fabric, spunbond nonwoven fabric, spunbond/meltblown/spunbond (SMS) nonwoven fabric, and the like. According to the embodiment, the front exterior top sheet 21 and the back exterior top sheet 31 are formed of SMS nonwoven fabric, and the front exterior back sheet 22, the back exterior back sheet 32, and the exterior center sheet 40 are formed of spunbond nonwoven fabric.

The front exterior top sheet 21 and the front exterior back sheet 22 are provided on the front side, and the front exterior top sheet 21 is placed between the absorbent main body 11 and the front exterior back sheet 22 in the thickness direction.

As illustrated in FIG. 3, a plurality of front elastic members 23 formed of, for example, elastic strings are arranged between the front exterior top sheet 21 and the front exterior back sheet 22 while being spaced apart vertically. A plurality of front elastic members 23 are arranged to overlap with the one end portion 11A of the longitudinal direction of the absorbent main body 11 in the thickness direction.

The front exterior back sheet 22 has a front folding section 22A having an upper vertical end portion folded to the lower side (inseam side). A plurality of front upper-end elastic members 24 formed of, for example, elastic strings are provided in a gap of the thickness direction of the front folding section 22A while being spaced apart vertically.

As illustrated in FIG. 2, a plurality of front elastic members 23 and a plurality of front upper-end elastic members 24 are provided along the horizontal direction. As the plurality of front elastic members 23 and the plurality of front upper-end elastic members 24 are compressed in the horizontal direction, they tighten the front waist of the wearer and improve fit. Note that the plurality of front elastic members 23 and a plurality of front upper-end elastic members 24 are not necessarily provided in the front waist section 2. For example, the front waist section 2 may be formed of elastic nonwoven fabric or the like expandable/shrinkable horizontally.

According to the embodiment, an interval between the front upper-end elastic members 24 adjacent in the vertical direction in the front waist section 2 is narrower than an interval between the front elastic members 23 adjacent in the vertical direction. Therefore, a plurality of wrinkles formed by compressing a plurality of front upper-end elastic members 24 in the horizontal direction have a size smaller than the size of a plurality of wrinkles formed by squeezing together a plurality of front elastic members 23 in the horizontal direction. Therefore, when the diaper 1 is worn, clearance from the wearer's skin is reduced in the vicinity of the back side of the waist opening 1HB (refer to FIG. 1) for a snug fit. As a result, it is possible to improve fit and prevent the diaper 1 from slipping off.

The back exterior top sheet 31 and the back exterior back sheet 32 are provided on the back side, and the back exterior top sheet 31 is placed between the absorbent main body 11 and the back exterior back sheet 32 in the thickness direction. As illustrated in FIG. 3, the back exterior top sheet 31 and the back exterior back sheet 32 are arranged separately from the front exterior top sheet 21 and the front exterior back sheet 22.

A plurality of back elastic members 33 are arranged between the back exterior top sheet 31 and the back exterior back sheet 32 and are spaced apart vertically. A plurality of back elastic members 33 are arranged to overlap with the other end portion 11B of the longitudinal direction of the absorbent main body 11 in the thickness direction.

Similar to the front exterior back sheet 22, the back exterior back sheet 32 has a back folding portion 32A having a vertical upper-end portion folded toward the lower side (inseam side), and a plurality of back upper-end elastic members 34 are provided in a gap of the thickness direction of the back folding portion 32A while being spaced apart vertically.

As illustrated in FIG. 2, a plurality of back elastic members 33 and a plurality of back upper-end elastic members 34 are provided along the horizontal direction, and the plurality of back elastic members 33 and the plurality of back upper-end elastic members 34 are compressed in the horizontal direction to tighten a back waist of the wearer and improve fit. Note that a plurality of back elastic members 33 and a plurality of back upper-end elastic members 34 are not necessarily provided in the back waist section 3. For example, the back waist section 3 formed of elastic nonwoven fabric or the like that expandable/shrinkable horizontally may be provided.

Similar to the front waist section 2, an interval between the back upper-end elastic members 34 adjacent in the vertical direction in the back waist section 3 is narrower than an interval of the back elastic members 33 adjacent in the vertical direction. Therefore, a plurality of wrinkles formed by compressing a plurality of back upper-end elastic members 34 in the horizontal direction have a size in the vertical direction smaller than the size of a plurality of wrinkles formed by compressing a plurality of back elastic members 33 in the horizontal direction. Therefore, when the diaper 1 is worn, clearance from the wearer's skin is reduced in the vicinity of the back side of the waist opening 1HB (refer to FIG. 1) for a snug fit. As a result, it is possible to improve fit and prevent the diaper 1 from slipping off.

As illustrated in FIG. 2, a plurality of front leg elastic members 25 are provided in the lower end portion of the front waist section 2 and in both sides of the absorbent main body 11 of the horizontal direction, and a plurality of back leg elastic members 35 are provided in the lower end portion of the back waist section 3 and in both sides of the absorbent main body 11 of the horizontal direction. A plurality of front leg elastic members 25 and a plurality of back leg elastic members 35 are arranged separately not to cross the absorbent main body 11 in the longitudinal direction. A plurality of front leg elastic members 25 and a plurality of back leg elastic members 35 are respectively provided to fit around the leg opening 1HL (refer to FIG. 1) to improve fit around the wearer's legs and prevent leakage of urine to the outside.

In FIG. 2, a plurality of front elastic members 23, a plurality of front upper-end elastic members 24, a plurality of front leg elastic members 25, a plurality of back elastic members 33, a plurality of back upper-end elastic members 34, and a plurality of back leg elastic members 35 are indicated by one-dotted chain lines.

Note that, in the unfolding state of FIG. 2, the diaper 1 has an expanded state. Here, the "expanded state" refers to a state in which the front waist section 2 and the back waist section 3 are expanded without wrinkles by stretching a plurality of front elastic members 23, a plurality of front upper-end elastic members 24, a plurality of front leg elastic members 25, a plurality of back elastic members 33, a plurality of back upper-end elastic members 34, and a plurality of back leg elastic members 35. A plurality of front elastic members 23, a plurality of front upper-end elastic members 24, a plurality of back elastic members 33, and a plurality of back upper-end elastic members 34 expand in the horizontal direction, and a plurality of front leg elastic members 25 and a plurality of back leg elastic members 35 expand in the horizontal direction and the vertical direction.

As illustrated in FIG. 3, the exterior center sheet 40 is arranged to link the front exterior top sheet 21 and the front exterior back sheet 22 and link the back exterior top sheet 31 and the back exterior back sheet 32 to prevent the absorbent main body 11 from being exposed to the outside.

(Configuration of Absorbent Main Body 11)

Next, a configuration of the absorbent main body 11 will be described with reference to FIGS. 2 to 4, 5A, and 5B.

Figure 4:
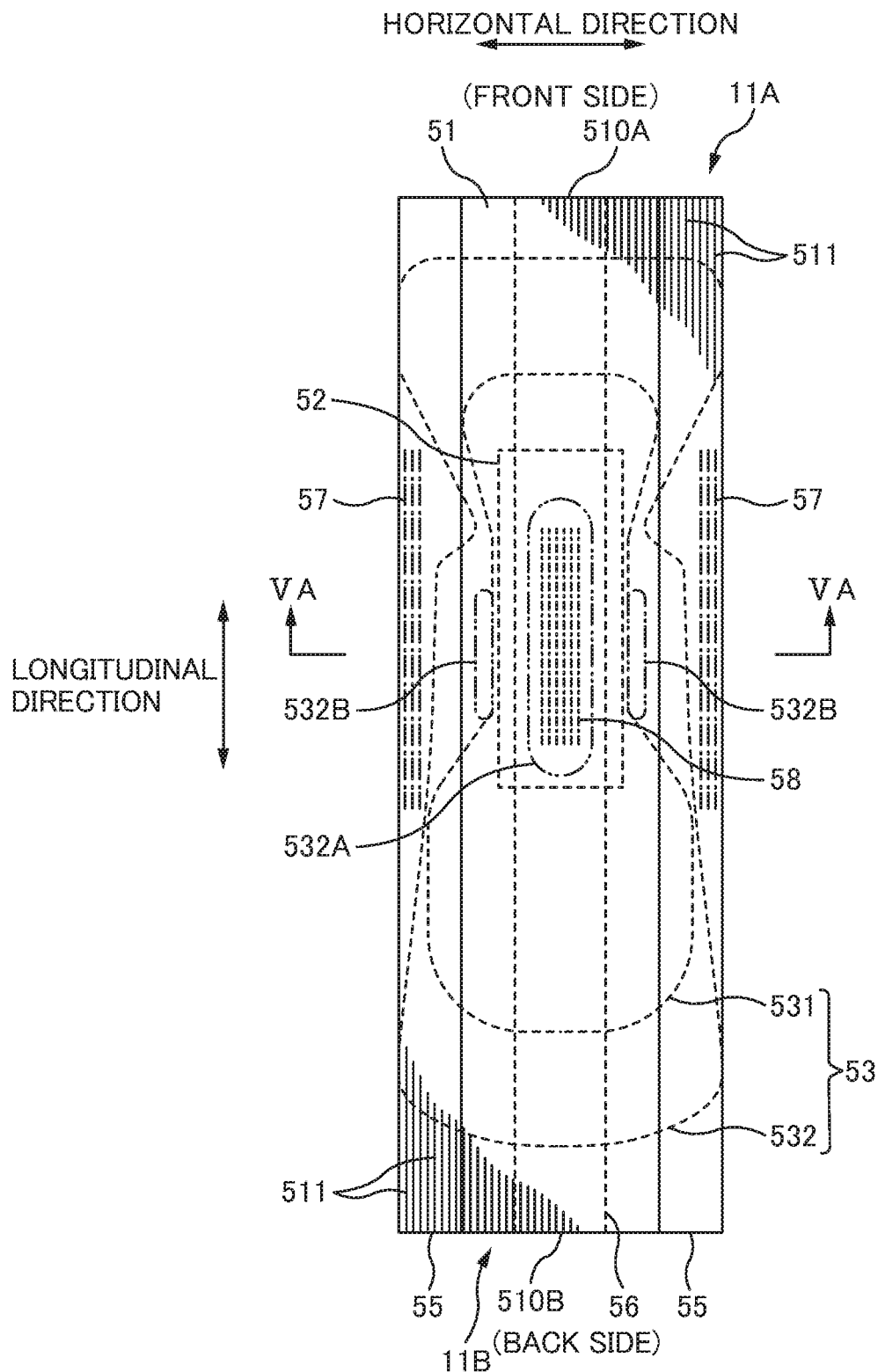
FIG. 4 is a schematic plan view illustrating an absorbent main body as seen from the skin side.
Figure 5A:
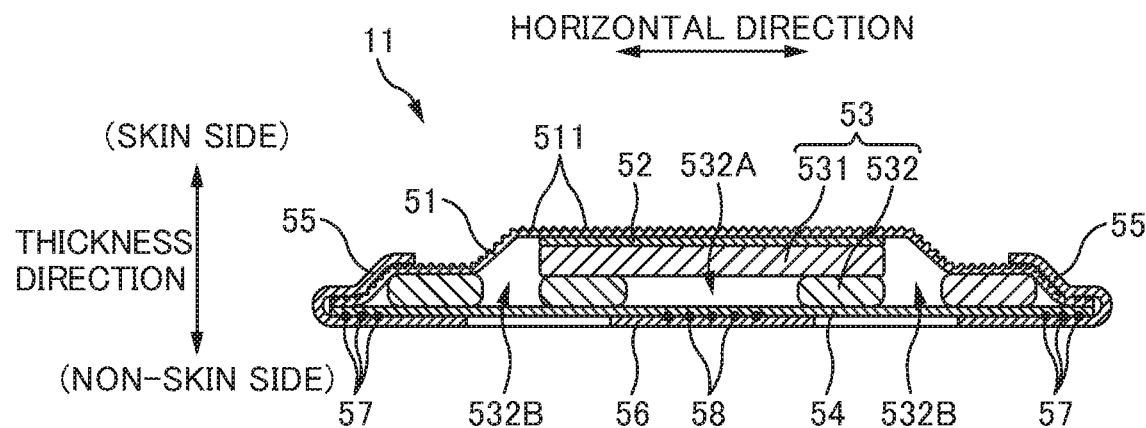
FIG. 5A is a cross-sectional view along a line VA-VA of FIG. 4.

FIG. 4 is a schematic plan view illustrating the absorbent main body 11 as seen from the skin side. FIG. 5A is a cross-sectional view along the line VA-VA of FIG. 4, and FIG. 5B is a cross-sectional view along the line VA-VA of FIG. 4 to illustrate a deformed state of the absorbent main body 11.

Figure 5B:
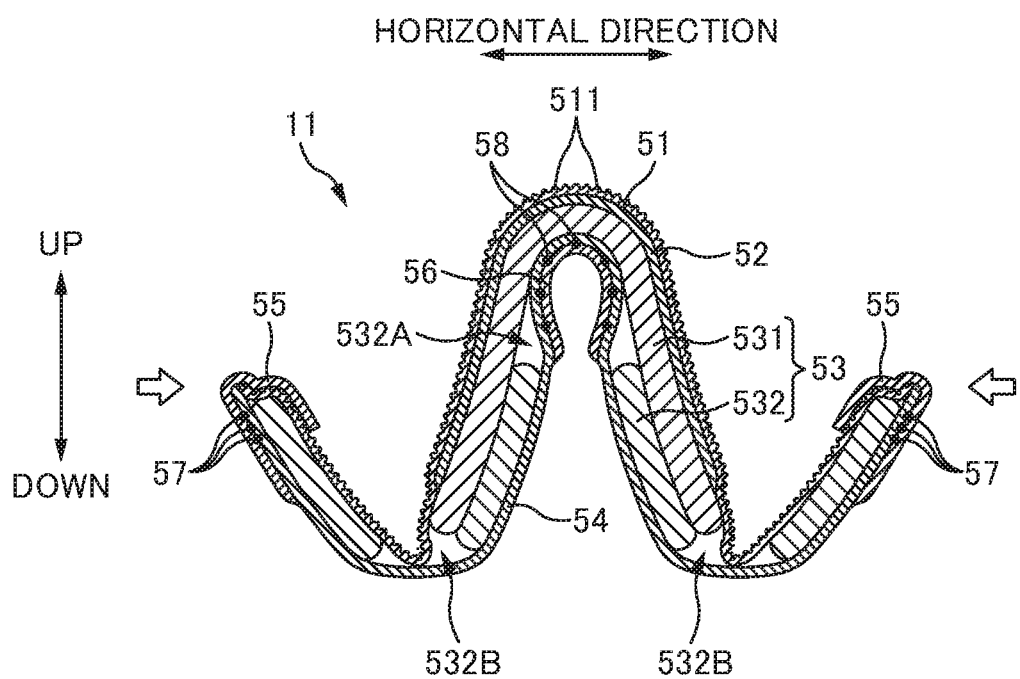
FIG. 5B is a cross-sectional view along the line VA-VA of FIG. 4 when the absorbent main body is in a deformed state.

As illustrated in FIGS. 3, 5A, and 5B, the absorbent main body 11 includes a top sheet 51, a second sheet 52, an absorbent core 53, a back sheet 54, a pair of side sheets 55, and a center elastic member cover sheet 56. Each member of the absorbent main body 11 is bonded to each other in the thickness direction using an adhesive such as a hot-melt adhesive.

The absorbent core 53 is a member for absorbing and holding a liquid such as urine and is formed of, for example, liquid absorbent fibers such as pulp fibers mixed with super-absorbent polymer (SAP). According to the embodiment, the absorbent core 53 includes a first core layer 531 formed in an hourglass shape, and a second core layer 532 having a size larger than the size of the first core layer 531 longitudinally and horizontally. The second core layer 532 is provided on the non-skin side of the first absorbent core 531.

In the second core layer 532, the center slit 532A along the longitudinal direction is provided in the center of the longitudinal direction and in the center of the horizontal direction, and a pair of side slits 532B along the longitudinal direction are provided in both sides of the horizontal direction of the center slit 532A while being spaced apart in the horizontal direction. Note that the absorbent core 53 does not necessarily have a two-layered structure including the first core layer 531 and the second core layer 532.

The top sheet 51 is provided on the skin side of the absorbent core 53 (first core layer 531) and serves as a liquid permeable skin-side sheet that can make contact with the wearer's skin when the diaper 1 is being worn. The top sheet 51 is formed, for example, of hydrophilic air-through nonwoven fabric, spunbond nonwoven fabric, or the like. According to the present embodiment, the top sheet 51 is formed of air-through nonwoven fabric. As illustrated in FIGS. 4, 5A, and 5B, the top sheet 51 has a plurality of protrusions 511 formed along the longitudinal direction and spaced apart in the horizontal direction.

According to the embodiment, a plurality of protrusions 511 protrude toward the skin side and are formed to continuously extend from one end 510A of the longitudinal direction of the top sheet 51 (of the absorbent main body 11) to the other end 510B. As a result, an air passage is formed. Therefore, the heat generated inside the diaper 1 can be easily discharged to the outside to improve air permeability. Note that the protrusions 511 are not necessarily formed to continuously extend from the one end 510A of the longitudinal direction of the top sheet 51 to the other end 510B. In FIG. 4, for simplicity, only apart of a plurality of protrusions 511 is illustrated.

As described above, a plurality of front elastic members 23 are placed to overlap with the one end portion 11A of the longitudinal direction of the absorbent main body 11 in the thickness direction. Therefore, a plurality of front elastic members 23 are provided in the one end portion 11A of the longitudinal direction of the absorbent main body 11 to cross a plurality of protrusions 511. Similarly, a plurality of back elastic members 33 are placed to overlap with the other end portion 11B of the longitudinal direction of the absorbent main body 11 in the thickness direction. Therefore, a plurality of back elastic members 33 is provided to cross a plurality of protrusions 511 in the other end portion 11B of the longitudinal direction of the absorbent main body 11.

Since a plurality of protrusions 511 is provided, the top sheet 51 has a high density portion (high density region 511D of FIG. 7B) and a low density portion. That is, the top sheet 51 has a density difference in the horizontal direction. The top sheet 51 having a plurality of protrusions 511 will be described in detail below.

The second sheet 52 is a liquid permeable sheet arranged between the absorbent core 53 and the top sheet 51 in the thickness direction and placed in the wearer's inseam. For example, the second sheet 52 is formed of hydrophilic air-through nonwoven fabric or the like. According to the embodiment, an average density of the entire second sheet 52 is higher than the average density of the horizontal direction of the top sheet 51.

Here, the "average density" is measured in the following way. The diaper 1 is laid on an observation table while an observation surface of the top sheet 51 (second sheet 52) faces upward, and a fiber surface is photographed using a predetermined measurement device (for example, a digital microscope, product number: VHX-100, produced by Keyence Corporation) to obtain a binary image of the fiber. In addition, a value obtained by dividing a spatial area of the binary image (the area of the region where no fiber is present: $\mu m^2$) by the number of spaces existing in the binary image is an average spatial area of the fiber (=spatial area/number of spaces), which corresponds to an average density of the top sheet 51 (second sheet 52).

A liquid such as urine tending to flow from a low density side to a high density side easily moves to the second sheet 52 as it passes through the top sheet 51. As a result, a liquid migration property inside the absorbent main body 11 is improved, and urine or the like is easily absorbed in the absorbent core 53. Therefore, it is possible to prevent accumulation of urine or the like on the top sheet 51 and more effectively suppress leakage of urine. Note that the average density of the second sheet 52 is not necessarily higher than the average density of the top sheet 51.

As illustrated in FIGS. 2 and 4, the second sheet 52 has a rectangular shape having a long side in the longitudinal direction and is formed to be smaller than the top sheet 51 horizontally and longitudinally. According to the embodiment, the second sheet 52 is formed to be smaller than the first core layer 531 of the absorbent core 53 longitudinally and horizontally. Note that the second sheet 52 may be smaller than the top sheet 51 at least horizontally.

As illustrated in FIG. 5A, the back sheet 54 is a liquid non-permeable non-skin-side sheet provided on the non-skin side of the absorbent core 53 and is formed of, for example, a polyethylene film or the like. A pair of leak-proof side sheets 55 are provided on both sides of the horizontal direction in the non-skin side of the back sheet 54 and formed of, for example, hydrophobic SMS nonwoven fabric or the like. A pair of side sheets 55 are bonded to the skin-side surface of the top sheet 51 such that the horizontal outer end portion is folded to face the skin side to respectively surround the horizontal outer end portion of the top sheet 51 and the horizontal outer end portion of the back sheet 54.

A plurality of longitudinally compressibly stretchable inseam-side leg elastic members 57 spaced apart in the horizontal direction are provided between the back sheet 54 and the side sheet 55. A plurality of inseam-side leg elastic members 57 are placed in both ends of the horizontal direction of the absorbent main body 11 to improve fit of the wearer's legs in cooperation with a plurality of front leg elastic members 25 and a plurality of back leg elastic members 35 (refer to FIG. 2) when the diaper 1 is worn.

In the non-skin side of the back sheet 54, a plurality of longitudinally compressibly stretchable center elastic members 58 spaced apart in the horizontal direction are provided in the longitudinal center inward of a plurality of inseam-side leg elastic members 57 in the horizontal direction. As illustrated in FIG. 5A, a plurality of center elastic members 58 are placed to overlap with a position of the center slit 532A of the second core layer 532 in the thickness direction.

In the non-skin side of the back sheet 54, a center elastic member cover sheet 56 for covering a plurality of center elastic members 58 from the non-skin side is arranged. The center elastic member cover sheet 56 is formed of, for example, hydrophobic spunbond nonwoven fabric or the like. As illustrated in FIG. 5A, the center elastic member cover sheet 56 is placed inward of a pair of side sheets 55 in the horizontal direction while being spaced apart in the horizontal direction from a pair of side sheets 55. As illustrated in FIGS. 2 and 4, the center elastic member cover sheet 56 is formed in a band shape extending from the one end portion 11A to the other end portion 11B in the longitudinal direction of the absorbent main body 11.

The absorbent main body 11 has a plurality of inseam-side leg elastic members 57 and a plurality of center elastic members 58 along the longitudinal direction. Therefore, a longitudinal compression difference between both ends and the center of the horizontal direction is reduced, and compression becomes uniform. As a result, it is possible to allow the absorbent main body 11 to make contact with a surface between the legs of the wearer and more effectively suppress leakage of the urine to the outside.

As illustrated in FIG. 5B, when the diaper 1 is being worn, a force is applied to the absorbent main body 11 inward from the outside in the horizontal direction due to the wearer's legs or the like (as indicated by the arrow in FIG. 5B). In this case, both sides of the horizontal direction of the center slit 532A of the absorbent main body 11 collapse downward with respect to the center slit 532A, and the outer sides of the horizontal direction of the pair of side slits 532B collapse upward with respect to the pair of side slits 532B. That is, the absorbent main body 11 is deformed such that its cross section has a W-shape.

This is because the center slit 532A and the pair of side slits 532B have a basis weight set to zero and do not have stiffness, so that they easily serve as the point of collapse in the thickness direction of the absorbent main body 11. As a result, it is possible to reduce a distance between the absorbent main body 11 and the excretory opening and fit the diaper to a wearer's somatotype in the inseam side. Therefore, it is possible to improve the fit of the diaper 1 when worn and prevent leakage of urine.

The pair of side slits 532B are a type of grooves provided in both sides of the second sheet 52 in the horizontal direction of the absorbent core 53 to extend along the longitudinal direction. The groove is not necessarily a slit penetrating in the thickness direction and having a basis weight of zero as long as a basis weight of the groove is smaller than a basis weight of the portion other than the groove of the absorbent core 53. In this case, stiffness of the absorbent core 53 decreases in the groove, and the thickness is also reduced. Therefore, the groove easily serves as the point of collapse of the thickness direction of the absorbent main body 11. Note that the center slit 532A and the pair of side slits 532B are not necessarily provided in the absorbent core 53.

(Configuration of Top Sheet 51)

Next, a configuration of the top sheet 51 of the absorbent main body 11 will be described in details with reference to FIGS. 6 to 10.

Figure 6:
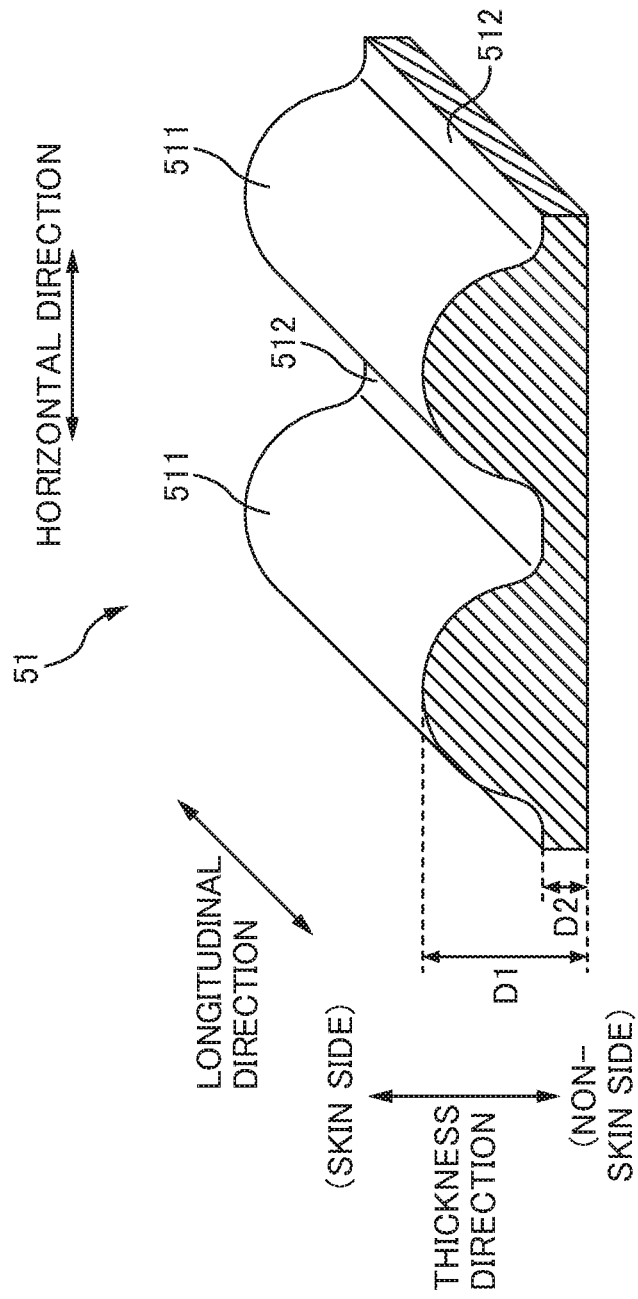
FIG. 6 is a partially enlarged perspective view illustrating protrusions and thin portions of the top sheet.
Figure 7A:
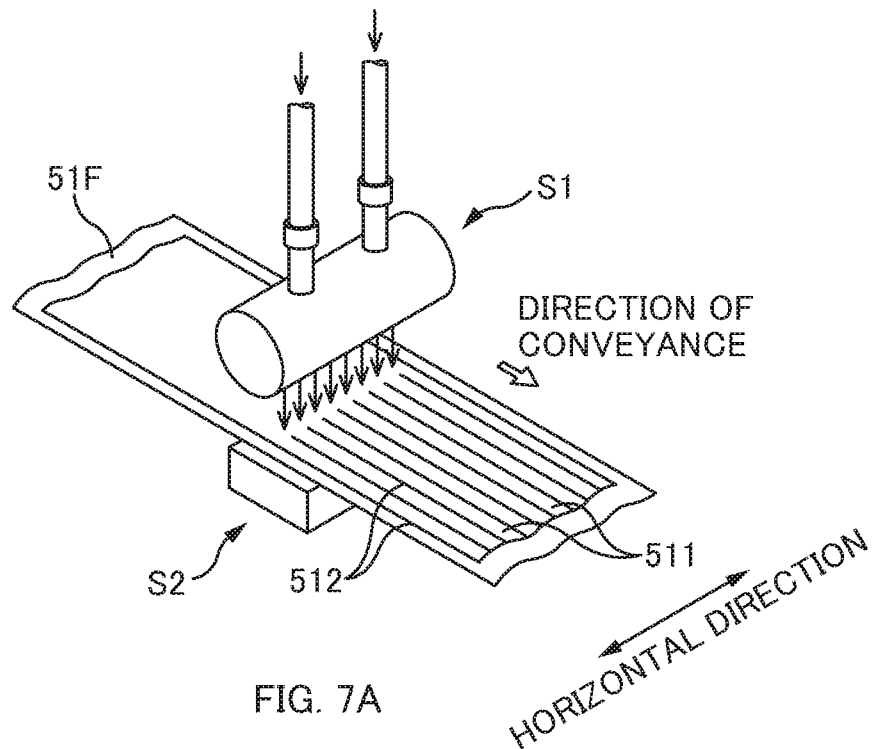
FIG. 7A is an explanatory diagram illustrating an injection process of a top sheet manufacturing process.
Figure 7B:
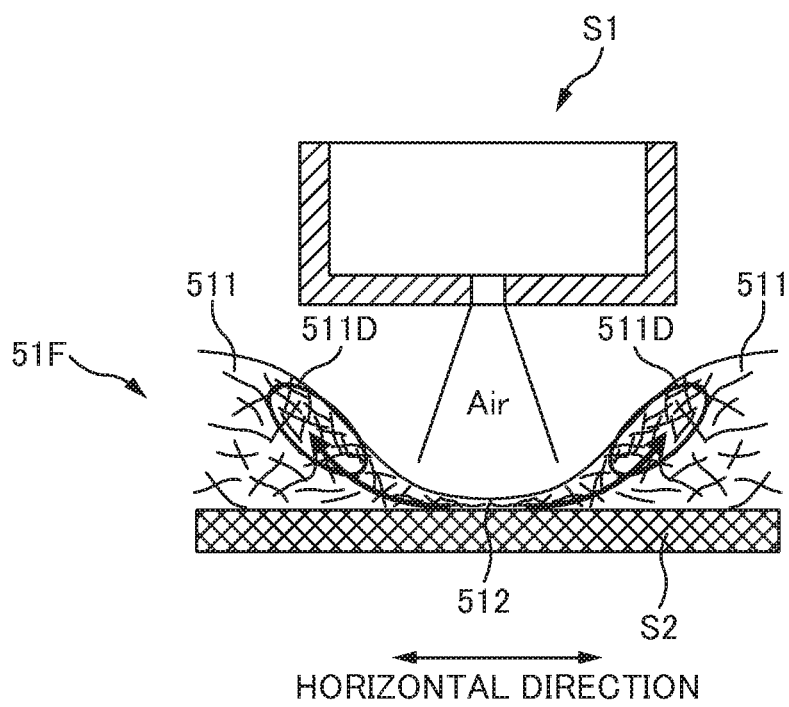
FIG. 7B is an explanatory diagram illustrating protrusions and thin portions formed in the injection process.
Figure 8A:
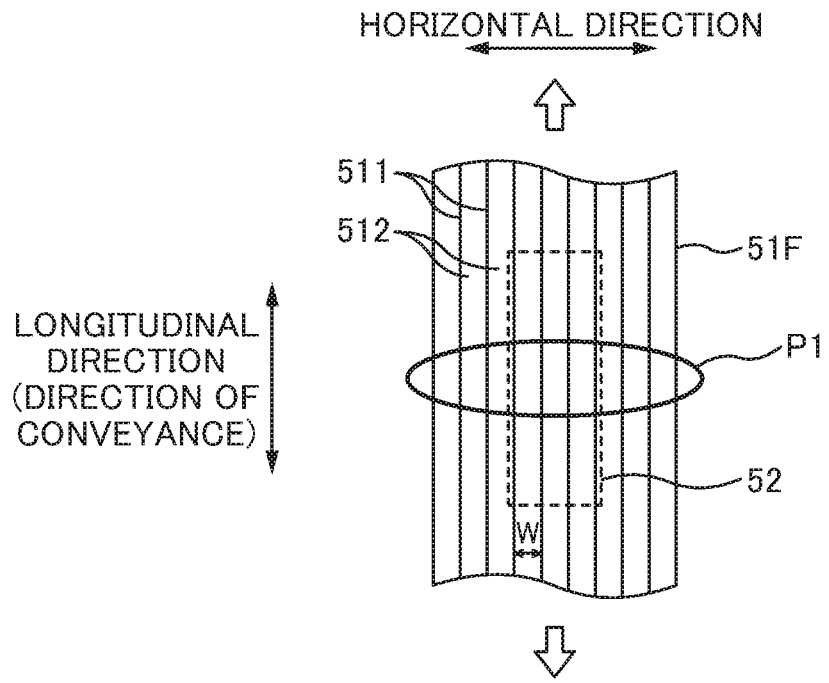
FIG. 8A is an explanatory diagram illustrating a state in which a second sheet is arranged on the top sheet in the top sheet manufacturing process.
Figure 8B:
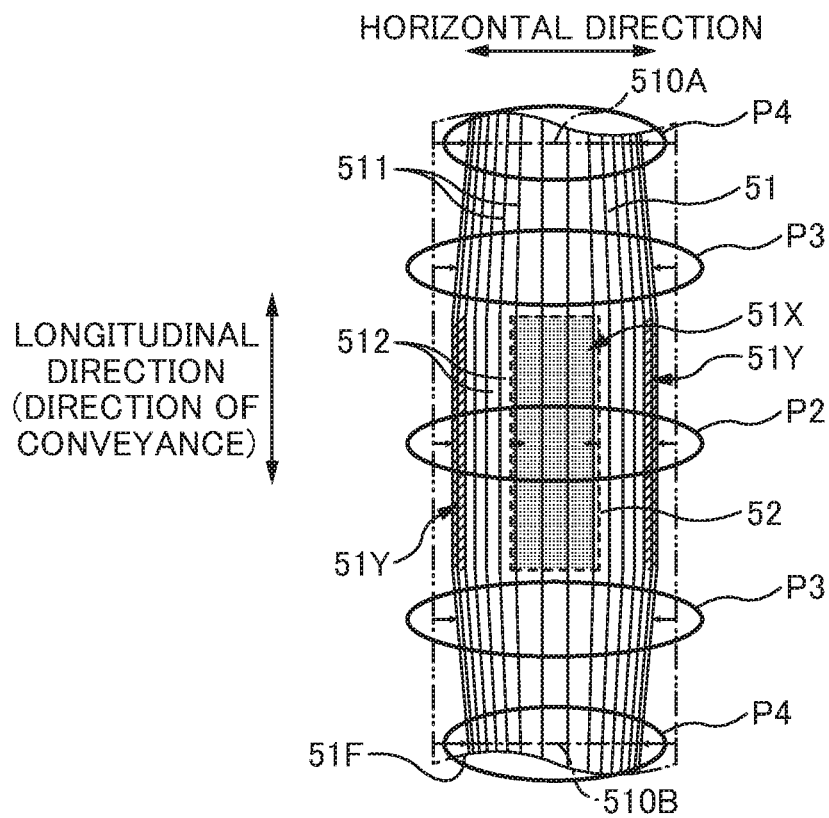
FIG. 8B is an explanatory diagram illustrating a state in which the top sheet where the second sheet is arranged is pulled in a longitudinal direction.
Figure 9A:
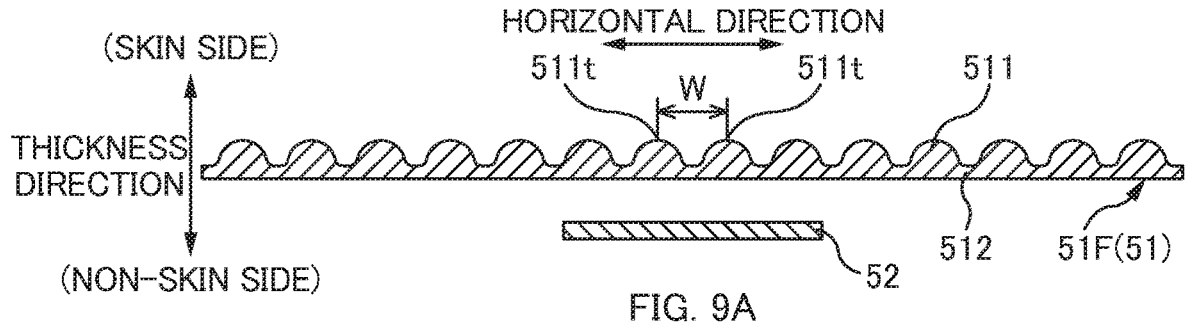
Figure 9B:
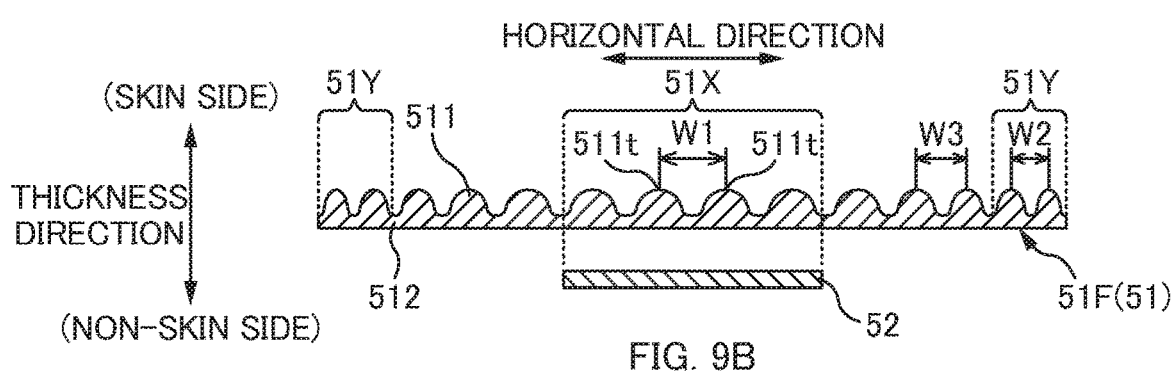
Figure 9C:
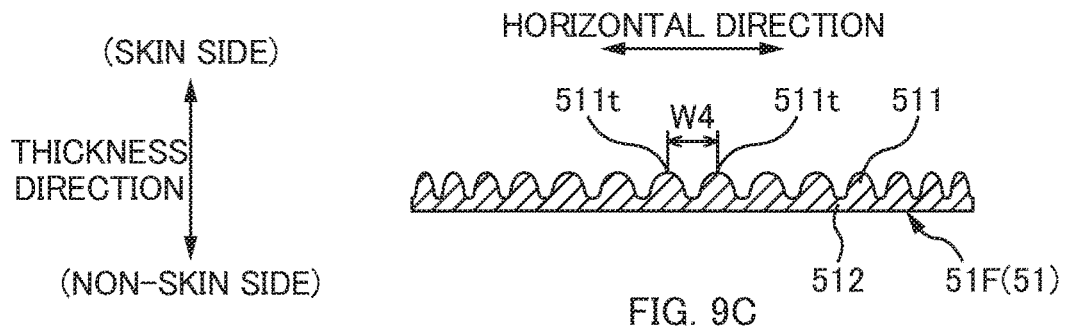
Figure 9D:
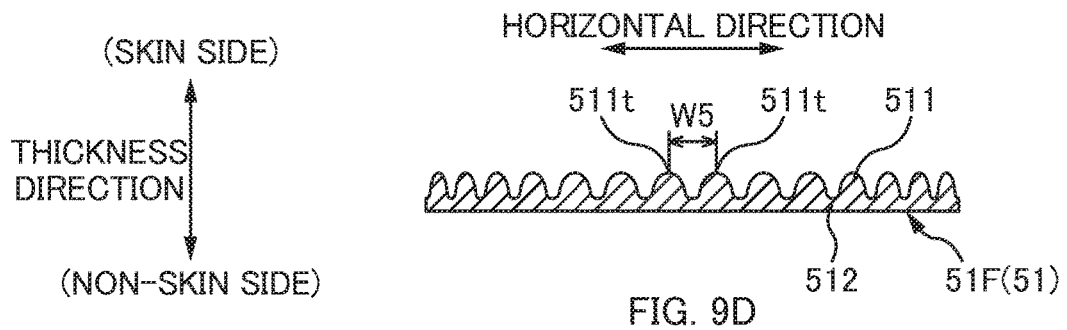
Figure 10A:
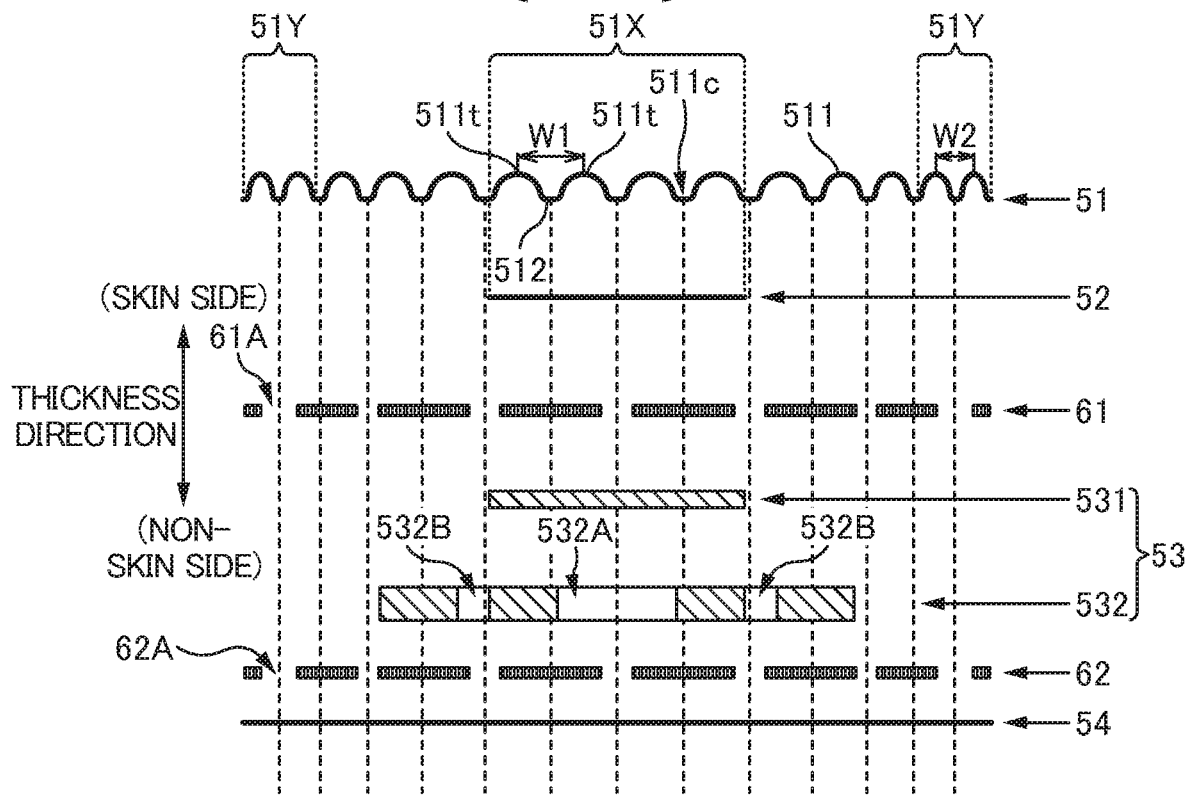
FIG. 10A is a schematic diagram illustrating a cross section of the absorbent main body.
Figure 10B:
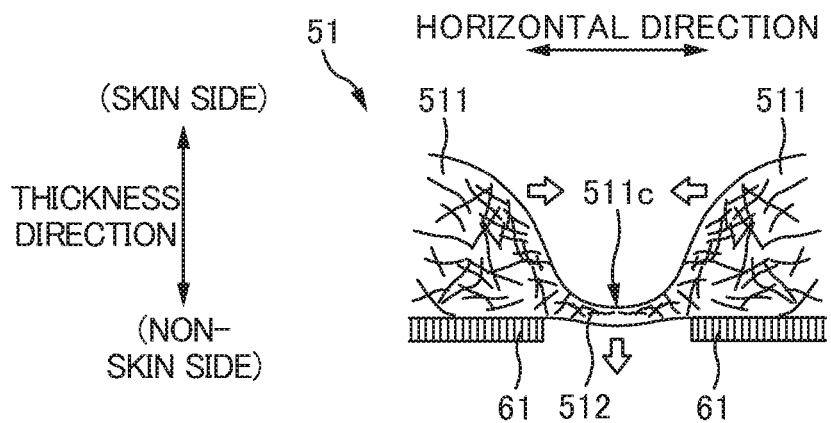
FIG. 10B is a schematic diagram illustrating a deformed state of the protrusion when the diaper is worn.

FIG. 6 is a partially enlarged perspective view illustrating configurations of the protrusions 511 and thin portions 512 of the top sheet 51 of the absorbent main body 11. FIG. 7A is an explanatory diagram for describing an injection process in a manufacturing process of the top sheet 51, and FIG. 7B is an explanatory diagram for describing how the protrusions 511 and the thin portions 512 are formed in the injection process. FIG. 8A is an explanatory diagram illustrating a state in which the second sheet 52 is arranged on the top sheet 51 in the manufacturing process of the top sheet 51, and FIG. 8B is an explanatory diagram illustrating a state in which the top sheet 51 where the second sheet 52 is arranged is pulled in the longitudinal direction. FIGS. 9A, 9B, 9C, and 9D are schematic cross-sectional views illustrating the top sheet 51 in the thickness direction, in which FIG. 9A illustrates a P1 portion of FIG. 8A, FIG. 9B illustrates a P2 portion of FIG. 8B, FIG. 9C illustrates a P3 portion of FIG. 8B, and FIG. 9D illustrates a P4 portion of FIG. 8B. FIG. 10A is a schematic diagram illustrating a cross section of the absorbent main body 11, and FIG. 10B is a schematic diagram illustrating a deformed state of the protrusion 511 when the diaper 1 is worn. Note that a plurality of inseam-side leg elastic members 57 and a plurality of center elastic members 58 are not illustrated in FIG. 10A for simplicity purposes.

As illustrated in FIG. 6, in the top sheet 51, a plurality of protrusions 511 are spaced apart in the horizontal direction, and the thin portions 512 are provided along the longitudinal direction between the protrusions 511 adjacent in the horizontal direction. Therefore, the top sheet 51 is configured such that the protrusions 511 and the thin portions 512 of the longitudinal direction alternate in the horizontal direction. In the thin portions 512, since the thickness D2 is smaller than the thickness D1 of the protrusion 511 (D2<D1), a gap between the protrusions 511 adjacent in the horizontal direction has a hollowed shape. That is, the top sheet 51 is an uneven sheet having an uneven skin-side surface.

According to the embodiment, the protrusion 511 has a substantially semicircular cross-sectional shape in the thickness direction and a curved skin-side surface. However, the shapes of the protrusions 511 and the thin portions 512 are not particularly limited. For example, the protrusion 511 may have a triangular cross-sectional shape in the thickness direction. In addition, the skin surface of the thin portion 512 may be a curvilinear surface curved toward the non-skin.

The plurality of protrusions 511 and the plurality of thin portions 512 are formed through an injection process as illustrated in FIG. 7A. In the injection process, a gas (air) is injected from the upside to a skin surface of a conveyed top-sheet member 51F (a sheet member cut in the later into the top sheet 51) using an injection device S1. As illustrated in FIG. 7B, in a portion where the gas is injected, fibers of the top-sheet member 51F move to be squeezed outward perpendicularly (horizontal direction) to a direction of conveyance. As a result, the thickness is reduced in this portion to form the thin portion 512. In addition, in both sides of the horizontal direction of this portion, the thickness increases due to the moving fibers to form the protrusions 511.

In this case, as illustrated in FIG. 7B, the fibers moving by the injected gas are easily concentrated on the sides facing the adjacent protrusions 511, and a portion having the highest fiber density in the top sheet 51 (the high density region 511D) is formed inside the protrusion 511. In this manner, by generating a difference of the fiber density inside the top sheet 51 (top-sheet member 51F), urine easily moves from the low fiber density portion to the high fiber density portion, so that solid components in urine can be trapped between the fibers. As a result, it is possible to suppress clogging caused by the solid components, prevent leakage of urine, and suppress unpleasantness for the wearer.

According to the embodiment, the top sheet 51 (top-sheet member 51F) is formed of air-through nonwoven fabric in which short fibers are not bonded to provide a relatively high degree of freedom. Therefore, a gap is easily formed between fibers, and clogging caused by solid components in urine is not easily generated.

According to the embodiment, since a placement surface of the support S2 that supports the conveyed top-sheet member 51F from the non-skin-side surface is flat, the non-skin-side surface of the top sheet 51 is a flat surface. Alternatively, the non-skin-side surface of the top sheet 51 is not necessarily a flat surface. In addition, by adjusting the number of injection nozzles, a size and pitch of the nozzle of the injection device S1, a temperature of the air injected from the injection nozzle, the amount of the injected air, a tension of the conveyed top sheet 51, and the like, it is possible to set the number of the protrusions 511, the number of the thin portions 512, the interval, the fiber density, and the like to desired ranges.

The fibers of the top-sheet member 51F (top sheet 51) are oriented in various directions. In the manufacturing process of the top sheet 51, the top-sheet member 51F is conveyed while it is pulled in the longitudinal direction (direction of conveyance) as indicated by the arrow in FIG. 8A. Accordingly, each fiber of the top-sheet member 51F is also pulled in the longitudinal direction. For this reason, the fibers directed to cross the longitudinal direction move toward the longitudinal direction, and the entire top-sheet member 51F is compressed in the horizontal direction by the movement of the longitudinal direction (refer to FIG. 8B). In FIG. 8B, the outer edge of the top-sheet member 51F before the top-sheet member 51F is compressed in the horizontal direction is indicated by two-dotted chain lines.

Since the top-sheet member 51F is formed of air-through nonwoven fabric as described above, each fiber of the top-sheet member 51F is not easily restrained in a predetermined direction, but exists in various directions. Therefore, if the top-sheet member 51F is pulled in the longitudinal direction, and each fiber is provided on the longitudinal direction, the top-sheet member 51F is easily compressed in the horizontal direction, compared to a top-sheet member formed of other types of nonwoven fabric.

The "state in which the top-sheet member 51F is compressed in the horizontal direction" refers to a state in which the compressed horizontal size is maintained without expanding until the horizontal size is returned to its original size (the size with no load before being pulled in the longitudinal direction) even when a force applied longitudinally is released from the top-sheet member 51F pulled longitudinally.

As the top-sheet member 51F is compressed in the horizontal direction, a horizontal pitch between a plurality of protrusions 511 formed in the top-sheet member 51F through the injection process is reduced, compared to a horizontal pitch W between the protrusions 511 formed when the top-sheet member 51F is not pulled in the longitudinal direction (refer to FIGS. 8A and 9A).

Here, the "horizontal pitch between the protrusions 511" refers to a horizontal distance between each apex 511t of the protrusions 511 adjacent in the horizontal direction (for example, W of FIG. 9A, W1, W2, and W3 of FIG. 9B, W4 of FIG. 9C, and W5 of FIG. 9D). Note that the apex 511t refers to a portion of the protrusion 511 closest to the skin side in the thickness direction.

As illustrated in FIGS. 8B and 9B, the top sheet 51 has an overlapping region 51X overlapping with the second sheet 52 in the thickness direction, and both end regions 51Y separated by a predetermined distance outward from the overlapping region 51X in the horizontal direction and provided to overlap with the overlapping region 51X in the longitudinal direction. In FIG. 8B, the second sheet 52 is indicated by the dotted line, and the overlapping region 51X and both end regions 51Y are hatched.

As illustrated in FIG. 8B, the second sheet 52 overlaps in the overlapping region 51X in the thickness direction. Therefore, the top sheet 51 is not easily compressed in the horizontal direction due to stiffness of the second sheet 52, and horizontal compression of the top sheet 51 in the overlapping region 51X per unit length is smaller than horizontal compression per unit length in both end regions 51Y. For this reason, as illustrated in FIG. 9B, the horizontal pitch W1 of the protrusion 511 in the overlapping region 51X is larger than the horizontal pitch W2 of the protrusion 511 in both end regions 51Y (W1>W2).

In the overlapping region 51X, due to stiffness of the second sheet 52, the protrusions 511 are not easily compressed in the horizontal direction even when the diaper 1 is worn. Therefore, it is possible to easily maintain the shape of the protrusion 511 and hold the density difference formed inside the protrusion 511. As a result, in the overlapping region 51X placed in the wearer's excretory opening, it is possible to easily maintain a function of suppressing clogging by filtering out solid components in urine and prevent leakage of urine.

Meanwhile, in both end regions 51Y, the horizontal pitch W2 of the protrusion 511 is smaller than the horizontal pitch W1 of the protrusion 511 in the overlapping region 51X (W2<W1), the number of the thin portions 512 per unit length of the horizontal direction is larger than the number of the thin portions 512 per unit length of the horizontal direction in the overlapping region 51X. Since the thin portion 512 has a thickness thinner than the thickness of the protrusion 511 as described above, the diaper 1 is easily deformable the thickness direction. Therefore, in both end regions 51Y, compared to the overlapping region 51X, the top sheet 51 is easily deformable the thickness direction, and the diaper 1 easily deforms to fit the shape of the wearer's inseam. As a result, in both end regions 51Y close to the wearer's legs, it is possible to improve fit by fitting the wearer's somatotype.

According to the embodiment, as illustrated in FIGS. 8B and 9B, the horizontal pitch of the protrusions 511 of the top sheet 51 gradually increases from both end regions 51Y toward the overlapping region 51X. Specifically, the horizontal pitch W2 of the protrusion 511 in both end regions 51Y is smaller than the horizontal pitch W3 of the protrusion 511 between both end regions 51Y and the overlapping region 51X in the horizontal direction (W2<W3), and the horizontal pitch W1 of the protrusion 511 in the overlapping region 51X is larger than the horizontal pitch W3 of the protrusion 511 between both end regions 51Y and the overlapping region 51X in the horizontal direction (W3<W1).

This is because a part of the top sheet 51 close to the overlapping region 51X in the horizontal direction is easily affected by the stiffness of the second sheet 52, and influence of the stiffness of the second sheet 52 decreases from the overlapping region 51X toward both end regions 51Y, so that horizontal compression of the top sheet 51 per unit length increases from the overlapping region 51X toward both end regions 51Y in the horizontal direction.

In this manner, as the horizontal pitch of the protrusions 511 gradually increases from both end regions 51Y toward the overlapping region 51X in the top sheet 51 (W2<W3<W1), the horizontal pitch of the protrusions 511 in both horizontal sides of the overlapping region 51X is not abruptly reduced, compared to the horizontal pitch W1 of the protrusion 511 in the overlapping region 51X. Therefore, it is possible to easily maintain the shape of the protrusion 511 in a part close to the overlapping region 51X even in both horizontal sides of the overlapping region 51X, and suppress clogging caused by solid components in urine.

Toward both end regions 51Y, the number of the thin portions 512 per unit length of the horizontal direction increases more than the number of the thin portions 512 per unit length of the horizontal direction in the overlapping region 51X. Therefore, it is possible to easily gradually collapse the top sheet 51 in the thickness direction and smoothly fit the diaper 1 to the shape of the wearer's inseam.

Although, in the top sheet 51 according to the embodiment, the horizontal pitch of the protrusions 511 has a relationship W2<W3<W1 from both end regions 51Y toward the overlapping region 51X for ease of manufacturing, such a relationship may be set differently. Alternatively, any relationship may be possible as long as the horizontal pitch W1 of the protrusion 511 in the overlapping region 51X is at least larger than the horizontal pitch W2 of the protrusion 511 in both end regions 51Y (W2<W1). In addition, the horizontal pitch relationship of the protrusion 511 in the horizontal direction of the top sheet 51 may be established in the setting of the manufacturing device or the like instead of using the horizontal compression of the top sheet 51.

Since the second sheet 52 is smaller than the top sheet 51 also in the longitudinal direction, one longitudinal end 510A and the other longitudinal end 510B of the top sheet 51 (hereinafter, simply referred to as a "one end 510A' and "the other end 510B") are not easily affected by the stiffness of the second sheet 52, but are easily compressed in the horizontal direction, compared to the overlapping region 51X. Therefore, as illustrated in FIG. 8B, in the overlapping region 51X, horizontal compression per unit length is smaller than horizontal compression per unit length in one end 510A and the other end 510B. For this reason, as illustrated in FIGS. 9B and 9D, the horizontal pitch W1 of the protrusion 511 in the overlapping region 51X is larger than the horizontal pitch W5 of the protrusion 511 in one end 510A and the other end 510B (W1>W5).

In other words, in one end 510A and the other end 510B, the horizontal pitch W5 of the protrusion 511 is smaller than the horizontal pitch W1 of the protrusion 511 in the overlapping region 51X (W5<W1). Therefore, the number of the thin portions 512 per unit length of the horizontal direction is larger than the number of the thin portions 512 per unit length of the horizontal direction in the overlapping region 51X, and collapse in the thickness direction is facilitated in one end 510A and the other end 510B compared to the overlapping region 51X. Therefore, it is possible to easily deform the diaper 1 to fit the wearer's front or back shape and the wearer's somatotype even for the front waist and the back waist of the wearer. Accordingly, it is possible to improve fit.

According to the embodiment, as illustrated in FIGS. 8B and 9B to 9D, the horizontal pitch of the protrusions 511 gradually increases from one end 510A and the other end 510B toward the overlapping region 51X. Specifically, in a region between the overlapping region 51X and one end 510A and in a region between the overlapping region 51X and the other end 510B (the P3 portion in FIG. 8B), the horizontal pitch W4 of the protrusion 511 is larger than the horizontal pitch W5 of the protrusion 511 in one end 510A and the other end 510B (the P4 portion in FIG. 8B) (W4>W5), and is smaller than the horizontal pitch W1 of the protrusion 511 in the overlapping region 51X (W4<W1).

Similar to the horizontal direction of the top sheet 51, this is because a region close to the overlapping region 51X in the longitudinal direction of the top sheet 51 is easily affected by the stiffness of the second sheet 52, and the influence of the stiffness of the second sheet 52 decreases from the overlapping region 51X toward one end 510A and the other end 510B, so that horizontal compression per unit length of the top sheet 51 increases from the overlapping region 51X toward one end 510A and the other end 510B in the longitudinal direction.

In this manner, as the horizontal pitch of the protrusions 511 gradually increases from one end 510A and the other end 510B of the longitudinal direction toward the overlapping region 51X in the top sheet 51 (W5<W4<W1), the horizontal pitch of the protrusions 511 in both longitudinal sides of the overlapping region 51X is not abruptly reduced, compared to the horizontal pitch W1 of the protrusion 511 in the overlapping region 51X. Therefore, it is possible to easily maintain the shape of the protrusion 511 in a part close to the overlapping region 51X even in both longitudinal sides of the overlapping region 51X, and suppress clogging caused by solid components in urine.

Toward one end 510A and the other end 510B, the number of the thin portions 512 per unit length of the horizontal direction increases more than the number of the thin portions 512 per unit length of the horizontal direction in the overlapping region 51X. Therefore, it is possible to easily gradually collapse the top sheet 51 in the thickness direction and smoothly fit the diaper 1 to the wearer's front or back shape. Note that, in FIG. 8B, one end 510A and the other end 510B are indicated by one-dotted chain lines.

Although, in the top sheet 51 of the embodiment, the horizontal pitch of the protrusions 511 has a relationship W5<W4<W1 from one end 510A and the other end 510B toward the overlapping region 51X for ease of manufacturing, such a relationship may be set differently. Alternatively, the horizontal pitch W1 of the protrusion 511 in the overlapping region 51X may be larger than at least the horizontal pitch W5 of the protrusion 511 in any one of one end 510A and the other end 510B (W5<W1). In addition, similar to the horizontal pitch relationship of the protrusion 511 in the horizontal direction, the horizontal pitch relationship of the protrusion 511 in the longitudinal direction of the top sheet 51 may be established in the setting of the manufacturing device or the like without using the horizontal compression of the top sheet 51.

As described above, according to the embodiment, the horizontal pitch relationship of the protrusion 511 is adjusted on the basis of the relationship of the horizontal compression of the top sheet 51 per unit length caused by horizontal compression of the top-sheet member 51F in the manufacturing process of the top sheet 51. Therefore, it is possible to change the horizontal pitch of the protrusions 511 without modifying the manufacturing device, for example, changing the setting of the injection nozzle of the injection device S1 or the like.

According to the embodiment, since the second sheet 52 is smaller than the top sheet 51 in the horizontal direction and in the longitudinal direction, the horizontal pitch of each protrusion 511 is different in both the horizontal direction and the longitudinal direction. Alternatively, the horizontal pitch W1 of the protrusion 511 in the overlapping region 51X may be at least larger than the horizontal pitch W2 of the protrusion 511 in both end regions 51Y (W1>W2).

As illustrated in FIG. 10A, the top sheet 51 and the absorbent core 53 are bonded in the thickness direction using a plurality of skin-side bonding portions 61 provided at intervals in the horizontal direction. An adhesive such as a hot-melt adhesive is applied to the skin-side bonding portion 61, and the skin-side bonding portion 61 has stiffness higher than the stiffness of the top sheet 51.

Here, assuming that a position horizontally intermediate between each apex 511t of the protrusions 511 adjacent in the horizontal direction is referred to as a "middle position 511c" (indicated by the dotted line in FIG. 10A), any one of a plurality of middle positions 511c does not overlap with the skin-side bonding portion 61 in the thickness direction in both end regions 51Y, but overlaps with a position of the gap 61A between the skin-side bonding portions 61 adjacent in the horizontal direction (hereinafter, simply referred to as a "gap 61A of the skin-side bonding portion").

Since the middle position 511c exists in the thin portion 512 having a thickness smaller than the thickness of the protrusion 511, the middle position 511c tends to serve as the point of collapse in the thickness direction of the top sheet 51. However, in both end regions 51Y, if the middle position 511c overlaps with a position of the skin-side bonding portion 61 having stiffness higher than the stiffness of the top sheet 51 in the thickness direction, the top sheet 51 is not easily deformable the thickness direction with respect to the middle position 511c.

In this regard, in the two end regions 51Y, the middle position 511c overlaps with the position of the gap 61A of the skin-side bonding portion in the thickness direction. As a result, it is possible to facilitate collapse of the top sheet 51 in the thickness direction with respect to the middle position 511c. Specifically, as indicated by the arrow in FIG. 10B, the protrusions 511 placed in both sides of the horizontal direction of the middle position 511c approach each other when the diaper 1 is worn. Therefore, it is possible to easily induce the collapse of the absorbent main body 11 in the thickness direction. As a result, it is possible to easily fit the absorbent main body 11 to the wearer's somatotype in the vicinity of the wearer's legs. Therefore, it is possible to improve fit of the diaper 1 when worn, prevent leakage of urine, and suppress unpleasant for the wearer.

In FIG. 10A, in each of both end regions 51Y, only one of the middle positions 511c overlaps with any one of the gaps 61A between the skin-side bonding portions in the thickness direction. Alternatively, without limitation thereto, for example, a plurality of middle positions 511c may respectively overlap with positions of the gaps 61A between a plurality of skin-side bonding portions in the thickness direction. Alternatively, a plurality of middle positions 511c may be placed in a position of any one of the gaps 61A of the skin-side bonding portions in the thickness direction.

As illustrated in FIG. 10A, the absorbent core 53 and the back sheet 54 are bonded in the thickness direction by a plurality of non-skin-side bonding portions 62 provided at intervals in the horizontal direction. Similar to the skin-side bonding portion 61, for example, an adhesive such as a hot-melt adhesive is applied to the non-skin-side bonding portion 62, and the non-skin-side bonding portion 62 has stiffness higher than the stiffness of the top sheet 51.

In both end regions 51Y, any one of a plurality of middle positions 511c does not overlap with the position of non-skin-side bonding portion 62 in the thickness direction, but overlaps with the position of the gap 62A between the non-skin-side bonding portions 62 adjacent in the horizontal direction (hereinafter, simply referred to as a "gap 62A of non-skin-side bonding portion). That is, according to the embodiment, in both end regions 51Y, any one of a plurality of middle positions 511c overlaps with the gap 61A of the skin-side bonding portion in the thickness direction, and overlaps with a position of the gap 62A of the non-skin-side bonding portion.

In this manner, in both end regions 51Y, any one of a plurality of middle positions 511c does not overlap with the skin-side bonding portion 61 and the non-skin-side bonding portion 62 having high stiffness in the thickness direction.

Therefore, the absorbent main body 11 is more easily deformable the thickness direction with respect to the middle position 511c.

In FIG. 10A, in each of both end regions 51Y, only one of the middle positions 511c overlaps with a position of any one gap 61A of the skin-side bonding portion in the thickness direction and one gap 62A of the non-skin-side bonding portion corresponding to the position of the gap 61A of the skin-side bonding portion. However, the invention is not limited thereto.

According to the embodiment, any one of a plurality of middle positions 511c overlaps with a position of the side slit 532B in the thickness direction. As a result, in addition to easiness of the collapse of the absorbent core 53 in the thickness direction caused by the side slit 532B described above, the top sheet 51 is easily deformable the thickness direction with respect to the middle position 511c. Therefore, the absorbent main body 11 is easily deformable the thickness direction in the vicinity of the wearer's legs to fit the wearer's somatotype.

In FIG. 10A, in each of both end regions 51Y, only one of the middle positions 511c overlaps with the position of the side slit 532B in the thickness direction. However, without limitation thereto, a plurality of middle positions 511c may be placed in the position of the side slit 532B in the thickness direction.

Note that the middle position 511c does not necessarily overlap with the position of the gap 61A of the skin-side bonding portion, the position of the gap 62A of the non-skin-side bonding portion, or the position of the side slit 532B in the thickness direction.

Second Embodiment

Figure 11:
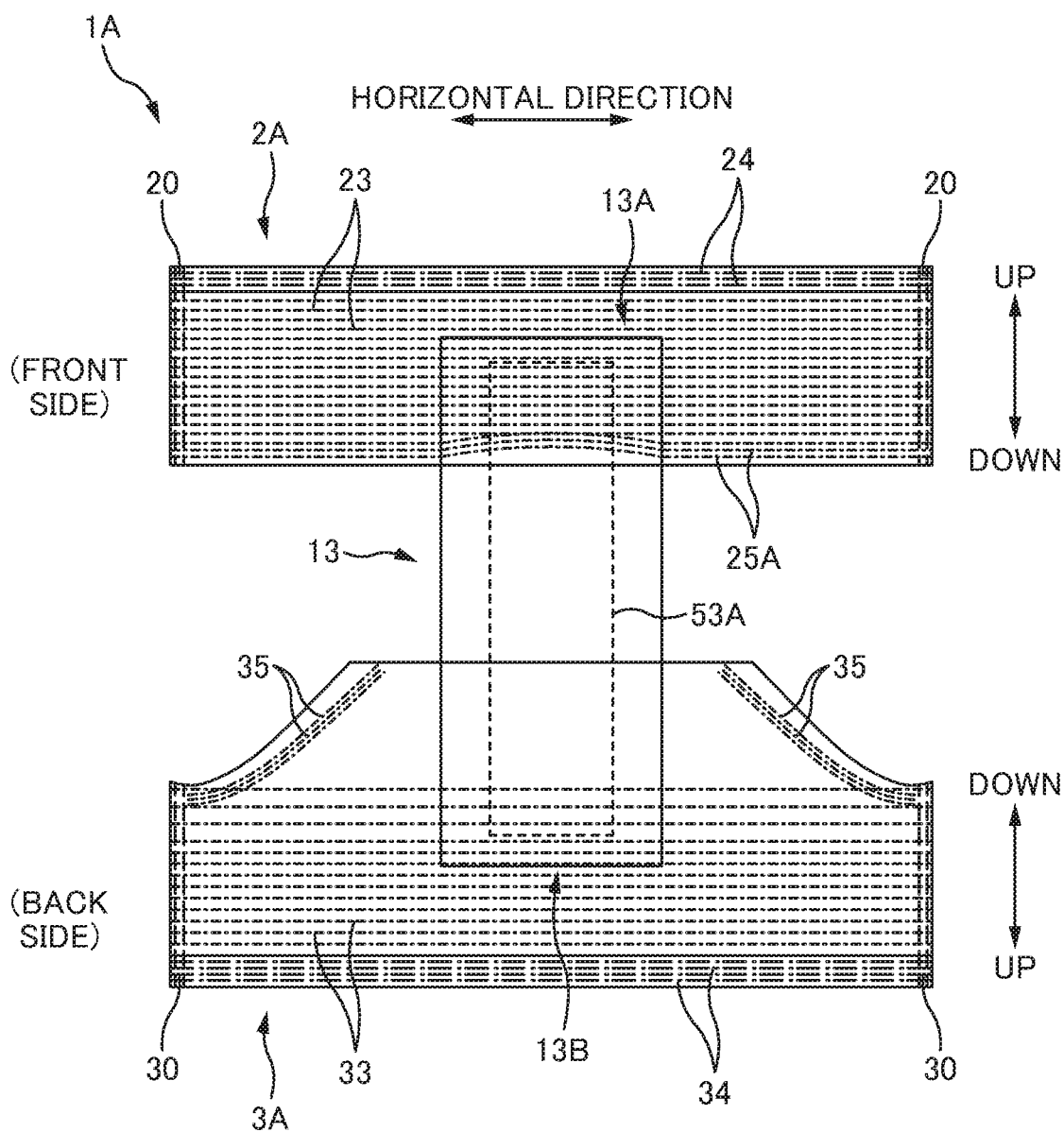
FIG. 11 is a schematic plan view illustrating an exemplary configuration of a diaper according to a second embodiment of the invention in an unfolded and expanded state as seen from a skin side.
Figure 12:
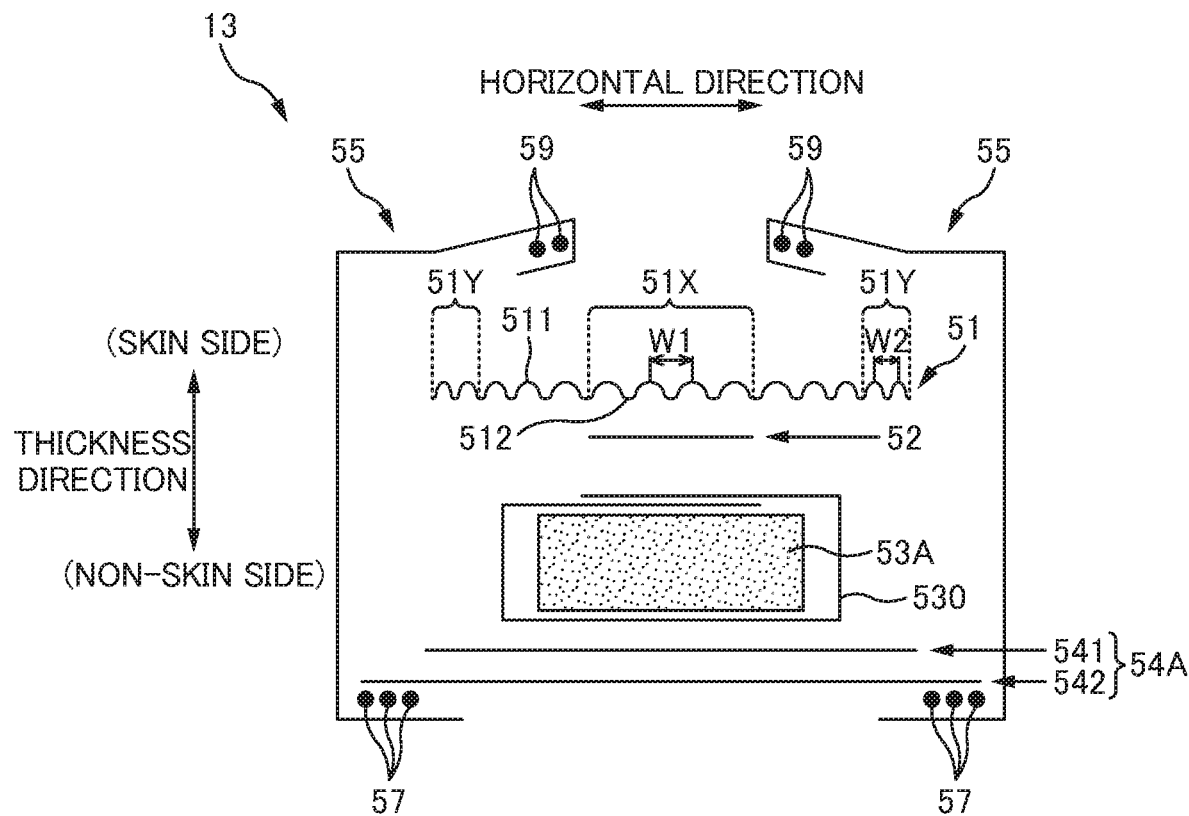
FIG. 12 is a schematic cross-sectional view illustrating an absorbent main body of the diaper according to the second embodiment in a thickness direction.

Next, a configuration of the diaper 1A according to the second embodiment of the invention will be described with reference to FIGS. 11 and 12. In FIGS. 11 and 12, like reference numerals denote like elements as for the components of the diaper 1 of the first embodiment and description thereof is omitted.

FIG. 11 is a schematic plan view illustrating an exemplary configuration of the diaper 1A according to the second embodiment in an unfolding and expanded state as seen from a skin side. FIG. 12 is a schematic cross-sectional view illustrating an absorbent main body 13 of the diaper 1A in the thickness direction.

The diaper 1A according to the embodiment is a so-called three-piece type pull-on diaper having a front waist section 2A, a back waist section 3A, and an absorbent main body 13. As illustrated in FIG. 11, while the diaper 1A is unfolded, the front waist section 2A is provided on one end portion 13A of the longitudinal direction of the absorbent main body 13, and the back waist section 3A is provided on the other end portion 13B of the longitudinal direction of the absorbent main body 13. That is, the absorbent main body 13 is stretched between the front waist section 2A and the back waist section 3A, which are spaced apart from each other.

The front waist section 2A is provided with a plurality of lower end side elastic member 25A along the horizontal direction arranged side by side and spaced apart vertically in the lower end portion under a plurality of front elastic members 23. The lower end side elastic member 25A is bent upward in a region overlapping with the absorbent main body 13 in the thickness direction. As a result, when the diaper 1A is worn, the front waist section 2A can be deformed in a cup shape in a portion close to the inseam. Therefore, it is possible to easily rest the sexual organ in the diaper 1A.

As illustrated in FIG. 12, the absorbent main body 13 has a top sheet 51, a second sheet 52, an absorbent core 53A, a back sheet 54A, and a pair of side sheets 55.

Unlike the configuration of the absorbent core 53 of the first embodiment, the absorbent core 53A does not have a two-layered structure, and the outer circumference is covered by a core-wrapping sheet 530. This core-wrapping sheet 530 is formed of, for example, tissues or the like and has a density higher than the fiber density of the second sheet 52. As a result, urine tends to flow from the skin side to the non-skin side in the thickness direction in order of the top sheet 51, the second sheet 52 having a fiber density higher than that of the top sheet 51, and the core-wrapping sheet 530 having a fiber density higher than that of the second sheet 52. Therefore, it is possible to improve a liquid migration property inside the absorbent main body 13.

The back sheet 54A has a first back sheet 541 formed from a liquid non-permeable sheet member such as a film, and a second back sheet 542 formed from a soft sheet member such as nonwoven fabric. The second back sheet 542 is provided on the non-skin side of the first back sheet 541 to prevent the first back sheet 541 from being exposed to the outside.

In a pair of side sheets 55, the outer end portion of the horizontal direction is folded toward the skin side, and a leading end of the folded portion is further folded toward the non-skin side. While a plurality of elastic members 59 are provided on this portion, the folded portion is bonded to the skin-side surface of the top sheet 51. As a result, a so-called barrier cuff is formed.

Since the diaper 1A according to the embodiment also has an uneven structure in the top sheet 51, it is possible to filter out solid components in urine and suppress clogging of the absorbent main body 13 caused by the solid component.

Similar to the diaper 1 of the first embodiment, the protrusions 511 are not easily compressed in the horizontal direction at least in the overlapping region 51X of the top sheet 51 due to stiffness of the second sheet 52 even when the diaper 1A is worn. Therefore, it is possible to easily maintain the shape of the protrusion 511 and hold a density difference formed inside the protrusion 511. As a result, in the overlapping region 51X placed in the excretory opening of the wearer, it is possible to easily maintain a function of suppressing clogging by filtering out solid components in urine and prevent leakage of urine.

Similar to the diaper 1 of the first embodiment, at least in both end regions 51Y, the horizontal pitch W2 of the protrusion 511 is smaller than the horizontal pitch W1 of the protrusion 511 in the overlapping region 51X (W2<W1). Therefore, the number of the thin portions 512 per unit length of the horizontal direction is larger than the number of the thin portions 512 per unit length of the horizontal direction in the overlapping region 51X. Therefore, in both end regions 51Y, compared to the overlapping region 51X, it is possible to facilitate collapse in the thickness direction and deform the diaper 1 to fit the wearer's inseam shape. As a result, it is possible to improve fit by fitting the diaper 1 to the wearer's somatotype in both end regions 51Y close to the wearer's legs.

Other Examples

While the embodiments have been described for facilitating understanding of the invention, they are not construed in a limitative manner. Various modifications and changes may be possible without departing from the spirit and scope of the invention, naturally encompassing equivalents thereof.

Although it is assumed that the diaper is worn on an elderly person in the aforementioned embodiments, the diaper may be worn on newborns or infants without a limitation.

While a pull-on disposable diaper has been described as an example of the absorbent article in the aforementioned embodiments, the invention may be employed in other purposes such as a sanitary napkin without a limitation. However, in the case of the sanitary napkin, it is difficult to think that the absorbent main body absorbs a menstrual bleeding amount enough to generate clogging, compared to the diaper. In addition, the effect that fit is improved by fitting the diaper to the shape of the inseam in the vicinity of the legs in a cup shape and suppressing clogging of the absorbent main body under an excretory opening is more advantageous when the invention is applied to a diaper in which a cup shape is formed using the wearer's inseam to allow the absorbent main body to absorb and hold urine, rather than a sanitary napkin that absorbs menstrual bleeding while allowing the top sheet to abut on a vaginal opening as an excretory opening.

REFERENCE SIGNS LIST 1, 1A diaper (absorbent article)
51 top sheet (skin-side sheet)
51X overlapping region
51Y both end regions
52 second sheet
53, 53A absorbent core
54, 54A back sheet (non-skin-side sheet)
61 skin-side bonding portion
62 non-skin-side bonding portion
510A one end
510B the other end
511 protrusion
511c middle position (position horizontally intermediate between each apex)
532B side slit (groove)

The invention claimed is:

1. An absorbent article having a longitudinal direction, a horizontal direction, and a thickness direction, the absorbent article comprising:
   an absorbent core to absorb a liquid;
   a liquid permeable skin-side sheet provided on a skin side of the absorbent core in the thickness direction; and
   a liquid permeable second sheet arranged between the absorbent core and the skin-side sheet in the thickness direction and to be placed in a wearer's inseam,
   wherein the skin-side sheet has a plurality of protrusions formed along the longitudinal direction and spaced apart in the horizontal direction,
   the second sheet is smaller than the skin-side sheet in the horizontal direction,
   the skin-side sheet has an overlapping region overlapping with the second sheet in the thickness direction, and two end regions separated by a predetermined distance outward from the overlapping region in the horizontal direction and provided to overlap with the overlapping region in the longitudinal direction,
   a horizontal pitch of the protrusions in the overlapping region of the skin-side sheet is larger than a horizontal pitch of the protrusions in the two end regions of the skin-side sheet,
   the skin-side sheet is compressed in the horizontal direction, and
   horizontal compression per unit length of the skin-side sheet in the overlapping region is smaller than compression per unit length of the skin-side sheet in the two end regions.

2. The absorbent article according to claim 1, wherein the horizontal pitch of the protrusions gradually increases from the two end regions toward the overlapping region in the skin-side sheet.

3. The absorbent article according to claim 1, wherein the second sheet is smaller than the skin-side sheet in the longitudinal direction, and
   the horizontal pitch of the protrusions in the overlapping region is larger than the horizontal pitch of the protrusions in at least one of one end and the other end of the longitudinal direction of the skin-side sheet.

4. The absorbent article according to claim 3, wherein the skin-side sheet has the horizontal pitch of the protrusions gradually increasing toward the overlapping region from at least one of the one end and the other end of the longitudinal direction.

5. The absorbent article according to claim 1, wherein the skin-side sheet and the absorbent core are bonded in the thickness direction by a plurality of skin-side bonding portions provided at intervals in the horizontal direction, and
   a position horizontally intermediate between each apex of any two protrusions adjacent in the horizontal direction among the plurality of protrusions does not overlap with a position of the skin-side bonding portion of the thickness direction in the two end regions of the skin-side sheet.

6. The absorbent article according to claim 5, further comprising a liquid non-permeable non-skin-side sheet provided on a non-skin side of the absorbent core,
   wherein the non-skin-side sheet and the absorbent core are bonded in the thickness direction by a plurality of non-skin-side bonding portions provided at intervals in the horizontal direction, and
   a position horizontally intermediate between each apex of any two protrusions adjacent in the horizontal direction among the plurality of protrusions does not overlap with a position of the non-skin-side bonding portion in the thickness direction in the two end regions of the skin-side sheet.

7. The absorbent article according to claim 1, wherein the absorbent core is provided with grooves extending along the longitudinal direction in both horizontal sides of the second sheet, and
   a basis weight of the groove is smaller than a basis weight of a portion other than the groove of the absorbent core.

8. The absorbent article according to claim 7, wherein a position horizontally intermediate between each apex of any two protrusions adjacent in the horizontal direction among the plurality of protrusions overlaps with a position of the groove in the thickness direction.

9. The absorbent article according to claim 1, wherein the skin-side sheet has a density difference in the horizontal direction, and
   an average density of the second sheet is higher than an average density of the skin-side sheet.

10. The absorbent article according to claim 1, wherein the skin-side sheet is formed of air-through nonwoven fabric.

11. An absorbent article having a longitudinal direction, a horizontal direction, and a thickness direction, the absorbent article comprising:
- an absorbent core to absorb a liquid;
- a liquid permeable skin-side sheet provided on a skin side of the absorbent core in the thickness direction; and
- a liquid permeable second sheet arranged between the absorbent core and the skin-side sheet in the thickness direction and to be placed in a wearer's inseam,
- wherein the skin-side sheet has a plurality of protrusions formed along the longitudinal direction and spaced apart in the horizontal direction,
- the second sheet is smaller than the skin-side sheet in the horizontal direction,
- the skin-side sheet has an overlapping region overlapping with the second sheet in the thickness direction, and two end regions separated by a predetermined distance outward from the overlapping region in the horizontal direction and provided to overlap with the overlapping region in the longitudinal direction,
- a horizontal pitch of the protrusions in the overlapping region of the skin-side sheet is larger than a horizontal pitch of the protrusions in the two end regions of the skin-side sheet,
- the second sheet is smaller than the skin-side sheet in the longitudinal direction,
- the horizontal pitch of the protrusions in the overlapping region is larger than the horizontal pitch of the protrusions in at least one of one end and the other end of the longitudinal direction of the skin-side sheet,
- the skin-side sheet is compressed in the horizontal direction, and
- horizontal compression per unit length of the skin-side sheet in the overlapping region is smaller than longitudinal compression per unit length of the skin-side sheet in at least one of the one end and the other end.

* * * * *